(12) United States Patent
Tian et al.

(10) Patent No.: US 11,905,534 B2
(45) Date of Patent: Feb. 20, 2024

(54) L-GLUTAMATE DEHYDROGENASE MUTANT AND APPLICATION THEREOF

(71) Applicant: Shanghai Qizhou Ziyue Biotechnology Co., Ltd., Shanghai (CN)

(72) Inventors: Zhenhua Tian, Shanghai (CN); Zhanbing Cheng, Shanghai (CN); Shaonan Ding, Shanghai (CN); Qi Jiao, Shanghai (CN); Wenxuan Xu, Shanghai (CN); Yao Huang, Shanghai (CN); Feng Jiang, Shanghai (CN)

(73) Assignee: SHANGHAI QIZHOU ZIYUE BIOTECHNOLOGY CO., LTD (CN)

( * ) Notice: Subject to any disclaimer, the term of this patent is extended or adjusted under 35 U.S.C. 154(b) by 0 days.

(21) Appl. No.: 17/531,081

(22) Filed: Nov. 19, 2021

(65) Prior Publication Data

US 2023/0183660 A1 Jun. 15, 2023

Related U.S. Application Data

(63) Continuation-in-part of application No. PCT/CN2020/089775, filed on May 12, 2020.

(30) Foreign Application Priority Data

May 23, 2019 (CN) .......................... 201910434350.1

(51) Int. Cl.
C12N 9/04 (2006.01)
C12N 9/06 (2006.01)
C12P 13/04 (2006.01)

(52) U.S. Cl.
CPC ......... *C12N 9/0016* (2013.01); *C12N 9/0028* (2013.01); *C12P 13/04* (2013.01); *C12Y 104/01004* (2013.01)

(58) Field of Classification Search
CPC .................................................. C12N 9/0016
See application file for complete search history.

(56) References Cited

U.S. PATENT DOCUMENTS

| | | | |
|---|---|---|---|
| 4,389,488 | A | 6/1983 | Grabley et al. |
| 5,130,246 | A | 7/1992 | Schulz et al. |
| 5,221,737 | A | 6/1993 | Bartsch et al. |
| 5,756,346 | A | 5/1998 | Willms et al. |
| 5,869,668 | A | 2/1999 | Knorr et al. |
| 6,936,444 | B1 | 8/2005 | Bartsch |
| 10,865,391 | B2 | 12/2020 | Yang et al. |
| 2020/0102546 | A1* | 4/2020 | Yang .............. C12Y 104/01003 |

FOREIGN PATENT DOCUMENTS

| | | |
|---|---|---|
| CN | 1053669 C | 6/2000 |
| CN | 1284858 C | 11/2006 |
| CN | 106978453 A | 7/2017 |
| CN | 107502647 A | 12/2017 |
| CN | 108588045 A | 9/2018 |
| EP | 0344683 A2 | 12/1989 |
| EP | 0382113 A1 | 8/1990 |

OTHER PUBLICATIONS

Studer. Residue mutations and their impact on protein structure and function: detecting beneficial and pathogenic changes. Biochem. J. (2013) 449, 581-594.*
Fransceus. J Ind Microbiol Biotechnol. May 2017;44(4-5):687-695.*
Sanavia. Computational and Structural Biotechnology Journal, vol. 18, 2020, pp. 1968-1979.*
Aug. 18, 2020 International Search Report issued in International Patent Application No. PCT/CN2020/089775.
Aug. 18, 2020 Written Opinion of the International Searching Authority issued in International Patent Application No. PCT/CN2020/089775.
Apr. 24, 2022 First Office Action issued in Chinese Patent Application No. 2019104343501.
Jul. 18, 2022 EESR issued in European Patent Application No. 20809767.5.
Dec. 13, 2018 (Dec. 13, 2018), "L. sphaerlcus glutamate dehydrogenase (LsGluDH) mutant A175G SEQ: 7.", XP002806945, retrieved from EBI accession No. GSP:BFT08446 Database accession No. BFT08446.
Dec. 13, 2018 (Dec. 13, 2018), "L. sphaericus glutamate dehydrogenase (LsGluDH) mutant V386A SEQ: 8.", XP002806946, retrieved from EBI accession No. GSP:BFT08447 Database accession No. BFT08447.
Yin Xinjian et al: "Efficient reductive amination process for enantioselective synthesis of L-phosphinothricin applying engineered glutamate dehydrogenase", Applied Microbiology and Biotechnology, Springer Berlin Heidelberg, Berlin/Heidelberg, vol. 102, No. 10, Mar. 16, 2018 (Mar. 16, 2018), pp. 4425-4433, XP036493130, ISSN: 0175-7598, DOI:10.1007/S00253-018-8910-Z.

(Continued)

*Primary Examiner* — Yong D Pak
(74) *Attorney, Agent, or Firm* — McCarter & English, LLP

(57) ABSTRACT

Disclosed in the present invention is an L-glutamate dehydrogenase mutant, the sequence of the L-glutamate dehydrogenase mutant being a sequence in which amino acid residue A at position 175 in SEQ ID NO: 1 is mutated to be G, and amino acid residue V at position 386 is mutated to be an amino acid residue having less steric hindrance. Further disclosed in the present invention is an application of the described L-amino acid dehydrogenase mutant in the preparation of L-glufosinate-ammonium or a salt thereof. When the L-glutamate dehydrogenase mutant of the present invention is used to prepare L-glufosinate-ammonium or a salt thereof, compared to an L-glutamate dehydrogenase mutant in which only position 175 or 386 is mutated, the specific enzyme activity is higher. Therefore, the action efficiency of the enzyme is improved, reaction costs are reduced, and industrial production is facilitated.

10 Claims, 6 Drawing Sheets

Specification includes a Sequence Listing.

(56) References Cited

OTHER PUBLICATIONS

Schulz et al: "Stereospecific production of the herbicide phosphinothricin (glufosinate) by transamination: isolation and characterization of a phosphinothricin—specific transaminase from *Escherichia coli*", Applied and Environmental Microbiology,, vol. 56, Jan. 1, 1990 (Jan. 1, 1990), pp. 1-6, XP00276930.

* cited by examiner

L-GLUTAMATE DEHYDROGENASE MUTANT AND APPLICATION THEREOF

CROSS REFERENCE TO RELATED APPLICATIONS

The present application is continuation-in-part of PCT/CN2020/089775, filed May 12, 2020, which claims priority from Chinese Patent Application CN201910434350.1, filed on May 23, 2019, the entire contents of which are hereby incorporated by reference.

REFERENCE TO SEQUENCE LISTING

The instant application contains a Sequence Listing which is being submitted in ASCII format via EFS-WEB, and is hereby incorporated by reference in its entirety. Said ASCII copy, created on Sep. 10, 2021, both of which are hereby incorporated by reference in their entireties.

TECHNICAL FIELD

The present invention relates to the field of biotechnology, particularly, relates to an L-glutamate dehydrogenase mutant and use thereof.

BACKGROUND OF THE INVENTION

Glufosinate (2-Amino-4-(hydroxymethylphosphinyl) butyric acid) is a broad-spectrum contact herbicide developed by Hoechst Inc. in the 1980s. At present, three major herbicides in the world are glyphosate, glufosinate and paraquat. Compared with glyphosate and paraquat, glufosinate has excellent herbicidal properties and less side effects. Glufosinate has two optical isomers, namely D-glufosinate and L-glufosinate, respectively. However, only L-glufosinate has herbicidal activity. Therefore, the development of a method for preparing L-glufosinate is of great significance for improving the atomic economy, reducing the cost of use and relieving environmental pressure.

At present, the method for preparing L-glufosinate mainly includes chiral resolution, chemical synthesis and biocatalysis.

Chiral resolution such as CN1053669C disclosed a method for preparing L-glufosinate by using quinine alkaloids as resolving agents, recrystallizing to obtain L-glufosinate quinine salt, which was then neutralized with acid. Meanwhile, 5-nitrosalicyaldehyde or 3, 5-dinitrosalicyaldehyde was used as a racemization reagent to racemize unreacted D-glufosinate to give DL-glufosinate, which was used for resolution reaction subsequently. However, this method requires expensive chiral resolution reagents and multi-step recrystallization, which is cumbersome and not ideal.

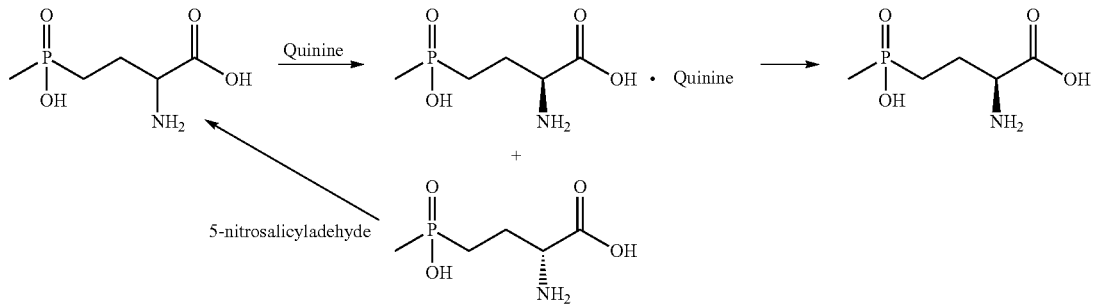

Chemical synthesis such as U.S. Pat. No. 6,936,444 disclosed that 2-acetamido-4-(hydroxymethylphosphinyl)-2-butenoic acid is asymmetrically hydrogenated by ruthenium catalysts to give L-2-acetamido-4-(hydroxymethylphosphinyl)-2-butyric acid, which can be deacetylated subsequently to give L-glufosinate. This method requires expensive metal catalysts, which increases the cost of synthesis, and produces heavy metal residues, thereby seriously polluting the environment.

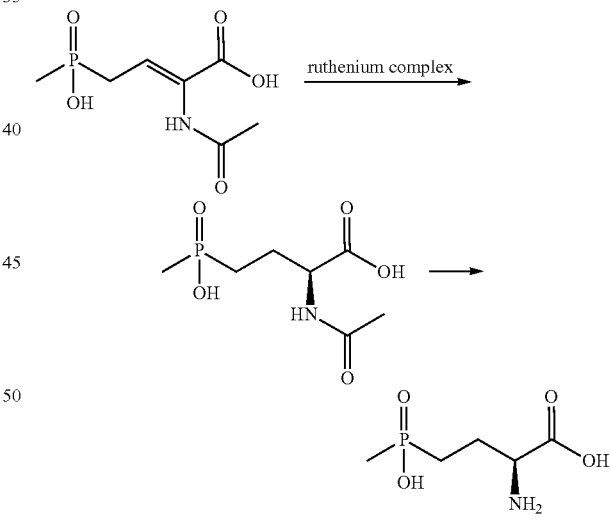

Compared with chiral resolution and chemical synthesis, biocatalysis has the advantage of strong specificity and mild reaction conditions, etc., and is a superior method for the production of L-glufosinate.

U.S. Pat. No. 4,389,488A described a method for producing L-glufosinate by using N-phenylacetyl-DL-glufosinate as substrate, and penicillin-G-acylase derived from *Escherichia coli* as catalyst. However, the synthesis cost of phenylacetyl glufosinate is relatively high, and a mixed solution of L-glufosinate, N-phenylacetyl-D-glufosinate and phenylacetic acid is obtained after the reaction, thereby requiring a strong acid cation exchange resin to separate L-glufosinate from the mixture, so the operation is complicated.

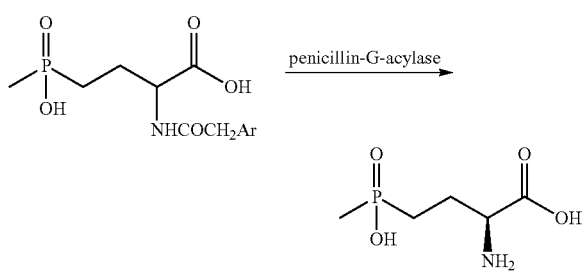

EP0382113A described a method for preparing L-glufosinate by catalytically cleaving the carboxylate of N-acetyl-glufosinate with acyltransferase, but enzyme therein is not specific to free N-acetyl-glufosinate, therefore, it's necessary for N-acetyl-glufosinate to be esterified, which increases the reaction steps and correspondingly increases the cost of production.

In other methods, 2-oxo-4-(hydroxymethyl phosphinyl) butyric acid (PPO) was used as substrate to prepare L-glufosinate by transaminase catalysis. Among them, U.S. Pat. No. 5,221,737A and EP0344683A described methods for preparing L-glufosinate from corresponding keto acid 4-(hydroxymethylphosphinyl)-2-oxo-butyric acid by transaminase derived from *Escherichia coli*, using glutamine acid as amino donor. The reaction system needs equal or excessive of glutamic acid as amino donor, which makes it difficult to purify the product. CN1284858C improved the above methods by using aspartic acid as amino donor, and giving L-glufosinate from corresponding keto acid 4-(hydroxymethylphosphinyl)-2-oxobutyric acid by aspartate aminotransferase, in which aspartic acid is converted to oxaloacetic acid. Oxaloacetic acid is unstable in aqueous medium and spontaneously decarboxylated to pyruvate, which can be removed by enzymatic reaction, making the reverse reaction impossible. Therefore, the reaction requires only equimolar amino donor and amino acceptor. However, the majority of the amino donors used in the method of using transaminase are amino acids, which has a relatively high cost.

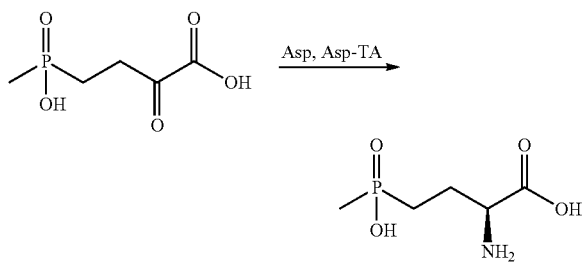

In addition, there is a method for preparing L-glufosinate using 2-oxo-4-(hydroxymethylphosphinyl) butyric acid (PPO) as substrate and amino acid dehydrogenase as catalyst. CN106978453A, for instance, used inorganic amino groups as donor, which makes the separation of the product simple and reduces the cost. However, the concentration range of substrate catalyzed by the enzyme in CN106978453A is only 10-100 mM, and the catalytic efficiency of amino acid dehydrogenase is limited.

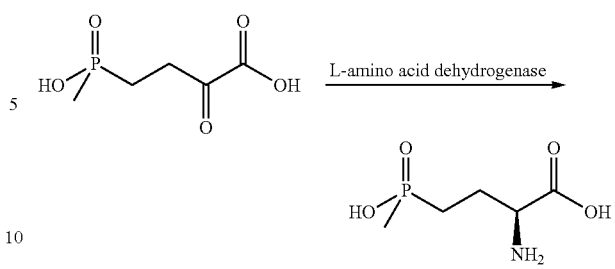

CN108588045A discloses the use of various glutamate dehydrogenase mutants in preparation of L-glufosinate, and discovers the glutamate dehydrogenase derived from *Pseudomonas putida* (NCBI Accession No.: NP_742836.1) has increased catalytic ability to PPO with mutating alanine at position 167 to glycine or mutating valine at position 378 to alanine. Then the mutants derived from other sources with mutation at positions homologous to position 167 and position 378 of a glutamate dehydrogenase were studied, and it is found that such mutants can also improve the catalytic ability of the glutamate dehydrogenase on PPO; however, combination mutations of these mutants with mutation on homologous sites of the glutamate dehydrogenases derived from other sources were not studied. In addition, although the two positions of the glutamate dehydrogenase derived from *Pseudomonas putida* were simultaneously mutated in the patent application, the enzyme activity of the obtained double-mutated mutant was only equivalent to that of the single mutant, and due to the unpredictability of the field of biology, the effect of mutants with double mutation sites is not necessarily better than that of their mutants with respective single-mutated mutation.

SUMMARY OF THE INVENTION

The technical problem to be solved by the present invention is the existing defect that L-glutamate dehydrogenase has a low catalytic efficiency in preparing L-glufosinate or salts thereof. Therefore, the present invention provides an L-glutamate dehydrogenase mutant and a use thereof in preparing L-glufosinate or salts thereof. Compared to the L-glutamate dehydrogenase mutant with mutating at single position (position 175 or 386), the present L-glutamate dehydrogenase mutant has a higher specific activity of enzyme when preparing an L-glufosinate or salts thereof, thereby increasing the efficiency of the action of the enzyme and reducing reaction costs, which are beneficial to industrial production.

The source of wildtype L-glutamate dehydrogenase used in the present invention is *Lysinibacillus sphaericus*, with the amino acid sequence of SEQ ID NO: 1, and Genbank Accession No. is WP_012293812.1. There is no mutant with mutation simultaneously at two sites of the glutamate dehydrogenase reported in prior art, and due to the unpredictability of the field of biology, the effect of mutants with double mutations is not necessarily better than that of their mutants with respective single mutation. Combination mutation was conducted by inventors on positions 175 and 386 of the wildtype enzyme targeting 2-oxo-4-(hydroxymethylphosphinyl) butyric acid (PPO) as the substrate, and inventors surprisingly found that when the amino acid residue A at position 175 is mutated to G, and the amino acid residue V at position 386 is mutated to an amino acid residue with smaller steric hindrance, the specific activity of enzyme of the resulted mutant to PPO as the substrate has significant increase.

The first technical solution that solves the above-mentioned technical problems in the present invention is provided as follows: an L-glutamate dehydrogenase mutant, the L-glutamate dehydrogenase mutant has a sequence obtained by mutating amino acid residue A at position 175 of SEQ ID NO: 1 to G, and, mutating amino acid residue V at position 386 to an amino acid residue with smaller steric hindrance; the L-glutamate dehydrogenase mutant has catalytic activity on 2-oxo-4-(hydroxymethylphosphinyl)-butyric acid or salts thereof.

Preferably, the amino acid sequence of the L-glutamate dehydrogenase mutant is set forth as SEQ ID NO: 7 or SEQ ID NO: 9.

Preferably, the nucleotide sequence of the L-glutamate dehydrogenase mutant is set forth as SEQ ID NO: 8 or SEQ ID NO: 10.

According to the present invention, the smaller steric hindrance means that compared with the amino acid residues of wild-type sequence, the mutated amino acid residues has smaller steric hindrance. The amino acids can be modified or unmodified natural amino acids; the present invention takes natural amino acids as an example.

The second technical solution that solves the above-mentioned technical problems in the present invention is provided as follows: an isolated nucleic acids, wherein the nucleic acids encode the L-glutamate dehydrogenase mutant described above.

Preferably, the nucleotide sequence encoding the nucleic acids is set forth as SEQ ID NO: 8 or SEQ ID NO: 10.

The third technical solution that solves the above-mentioned technical problems in the present invention is provided as follows: a recombinant expression vector comprising the nucleic acids described above.

The fourth technical solution that solves the above-mentioned technical problems in the present invention is provided as follows: a transformant comprising the nucleic acids or the recombinant expression vector described above.

The fifth technical solution that solves the above-mentioned technical problems in the present invention is provided as follows: a method for preparing L-glufosinate salt, which comprises the following steps: 2-oxo-4-(hydroxymethylphosphinyl) butyrate is subjected to an amination reaction to obtain an L-glufosinate salt in the presence of a reaction solvent, an L-glutamate dehydrogenase mutant, an inorganic amino donor and a reduced coenzyme NADPH (Nicotinamide adenine dinucleotide phosphate).

In the preparation method, except for the L-glutamate dehydrogenase mutant which is obtained by the present invention, the other raw materials, reaction steps and conditions can be conventional in the art. For details, please refer to the above-mentioned CN106978453A and the patent application of the applicant with application number CN201810162629.4.

The method for preparing the L-glufosinate salt can further comprises the following steps: a D-glufosinate salt is subjected to an oxidation reaction to obtain the 2-oxo-4-(hydroxymethylphosphinyl) butyrate in the presence of a D-amino acid oxidase (DAAO).

In the oxidation reaction, the cation of the D-glufosinate salt can be a cation of conventionally used in the art, such as ammonium ion, sodium ion and/or potassium ion. It can also be any cation of the buffer used.

In the oxidation reaction, the D-glufosinate salt can have a form of existing alone, or, coexisting with L-glufosinate salt (the L-glufosinate salt can not react at this time), e.g.: a D-type enriched glufosinate salt (i.e., the content of D-type enantiomer is more than 50%, even pure D-glufosinate salt), an L-type enriched glufosinate salt (i.e., the content of L-glufosinate is more than 50%, excluding pure L-glufosinate salt) or a racemic glufosinate salt, etc.

In the oxidation reaction, the D amino acid oxidase (DAAO) can be in a concentration of conventional in the art, preferably of 0.6-6 U/mL, more preferably of 1.8 U/mL.

In the oxidation reaction, the D-glufosinate salt can be in a concentration conventionally used in the art, preferably 100-600 mM, more preferably 200 mM.

The oxidation reaction can also be performed in the presence of catalase.

The oxidation reaction can also be performed under a condition of ventilation. The ventilation is preferably introducing air or oxygen; the rate of the ventilation is preferably 0.5-1 VVM.

In the present invention, the air can be the air conventionally used in the art, which generally contains oxygen, and the oxygen contained has the content conventionally used in the art. It is oxygen in the air that participates in the reaction.

When the oxidation reaction is performed under aeration condition, the oxidation reaction can also be performed in the presence of a defoamer.

In the oxidation reaction, the reaction system is in a pH of preferably 7-9, more preferably 8. The pH can be achieved by using a buffer. The pH can also be adjusted by using alkali (or alkali solution). The buffer is preferably a phosphate buffer or a Tris-HCl buffer, and the phosphate buffer is preferably a disodium hydrogen phosphate-sodium dihydrogen phosphate buffer or a dipotassium hydrogen phosphate-potassium dihydrogen phosphate buffer. The alkali solution is preferably ammonia.

In the oxidation reaction, the reaction system can be performed at a conventional temperature in the art, preferably 20-50° C., more preferably 20° C.

The oxidation reaction and the amination reaction can be performed separately or simultaneously (in the same reaction system). The simultaneously means that: in the presence of D-amino acid oxidase (DAAO), L-glutamate dehydrogenase mutant, inorganic amino donor and reduced coenzyme NADPH, a D-glufosinate salt is subjected to an oxidation reaction and an amination reaction to obtain an L-glufosinate salt.

In the amination reaction, the cation of the L-glufosinate salt can be a cation conventionally used in the art, such as an ammonium ion, a sodium ion and/or a potassium ion. It can also be the cation of the buffer used.

In the amination reaction, the cation of the 2-oxo-4-(hydroxymethylphosphinyl) butyrate can be a cation conventionally used in the art, such as an ammonium ion, a sodium ion and/or a potassium ions etc. It can also be the cation of the buffer used.

In the amination reaction, the L-glutamate dehydrogenase mutant can be in a conventional dosage in the art, for example, 0.05-3 U/mL, preferably 0.1-1 U/mL, such as 0.23 U/mL.

In the amination reaction, the inorganic amino donor can be in a conventional concentration in the art, for example, 100-2000 mM, preferably 200 mM.

In the amination reaction, the 2-oxo-4-(hydroxymethylphosphinyl) butyrate is in a concentration of 100-600 mM, preferably 200 mM.

In the amination reaction, the 2-oxo-4-(hydroxymethylphosphinyl) butyrate can be a conventional dosage in the art, and the mass ratio of the reduced coenzyme NADPH to the 2-oxo-4-(hydroxymethylphosphinyl) butyrate is 1:100-1:20000, preferably 1: 1000-1:15000, more preferably 1:5000.

In the amination reaction, the inorganic amino donor is one or more of ammonia, ammonium sulfate, ammonium chloride, diammonium hydrogen phosphate, ammonium acetate, ammonium formate and ammonium bicarbonate.

In the amination reaction, the reaction can be performed at temperatures conventionally used in the art. In order to ensure the catalytic efficiency of the L-glutamate dehydrogenase mutant, the amination reaction is performed at a temperature of preferably 20-50° C., more preferably 37° C. When the amination reaction is performed at a temperature of lower than 20° C., the speed of amination reaction is slow; when the amination reaction is performed at a temperature of higher than 50° C., the enzyme will be irreversibly denatured and inactivated.

In the amination reaction, the solvent of the reaction is water.

In the method, the amination reaction is performed at a pH of preferably 7-9, more preferably 8.5. The pH can be adjusted by using a buffer. The pH can also be adjusted by using alkali (or alkali solution). The buffer is preferably a phosphate buffer or a Tris-HCl buffer, and the phosphate buffer is preferably a disodium hydrogen phosphate-sodium dihydrogen phosphate buffer or a dipotassium hydrogen phosphate-potassium dihydrogen phosphate buffer. The alkali solution is preferably ammonia.

The method for preparing the L-glufosinate salt also comprises the following steps: an oxidized coenzyme NADP$^+$ is subjected to a reduction reaction to obtain the reduced coenzyme NADPH in the presence of a dehydrogenase (e.g., glucose dehydrogenase, alcohol dehydrogenase or formate dehydrogenase, etc.) and a hydrogen donor (e.g., glucose, isopropanol or formate, etc.).

In the reduction reaction, the dehydrogenase has a one-to-one correspondence with the hydrogen donor, for example:

When the dehydrogenase is an alcohol dehydrogenase, the hydrogen donor is an isopropanol;
When the dehydrogenase is a glucose dehydrogenase, the hydrogen donor is a glucose;
When the dehydrogenase is a formate dehydrogenase, the hydrogen donor is a formate.

In the reduction reaction, the dehydrogenase can be of conventional dosage in the art, preferably 0.6-6 U/mL, more preferably 2 U/mL.

In the reduction reaction, the hydrogen donor can be of conventional concentration in the art, preferably 100-1000 mM, more preferably 240 mM.

In the reduction reaction, the oxidized coenzyme NADP$^+$ can be of conventional concentration in the art.

In the reduction reaction, the reduction reaction is performed at a pH of preferably 7-9, more preferably 8.5. The pH can be adjusted by using a buffer. The pH can also be adjusted by using alkali (or alkali solution). The buffer is preferably a phosphate buffer or a Tris-HCl buffer, etc., and the phosphate buffer is preferably a disodium hydrogen phosphate-sodium dihydrogen phosphate buffer or a dipotassium hydrogen phosphate-potassium dihydrogen phosphate buffer, etc. The alkali solution is preferably ammonia.

In the reaction system, the reduction reaction can be performed at a temperature conventionally used in the art, preferably 20-50° C., more preferably 37° C.

The reduction reaction and the amination reaction can be performed separately or simultaneously (in the same reaction system). When performed simultaneously, as shown in the preferred embodiment of the present invention, 2-oxo-4-(hydroxymethylphosphinyl) butyrate is subjected to an amination reaction (the reduction reaction of NADP$^+$ exists at the same time) to obtain an L-glufosinate salt in the presence of glucose dehydrogenase, glucose, oxidized coenzyme NADP$^+$, L-glutamate dehydrogenase mutant and inorganic amino donor.

When the reduction reaction and the amination reaction are performed simultaneously, the NADPH used in the amination reaction can be generated cyclically by the reduction reaction. The oxidized coenzyme NADP$^+$ can be of conventional concentration in the art, and in order to ensure that the reaction can be conducted normally, the mass ratio of the oxidized coenzyme NADP$^+$ to the 2-oxo-4-(hydroxymethylphosphinyl) butyrate is 1:100-1:20000, preferably 1: 1000-1:15000, more preferably 1:5000.

The reduction reaction, the oxidation reaction and the amination reaction can be performed separately or simultaneously (in the same reaction system). When performed simultaneously, as shown in the preferred embodiment of the present invention, a D-glufosinate salt is subjected to an oxidation reaction and an amination reaction (a reduction reaction of NADP$^+$ exists simultaneously) to obtain an L-glufosinate salt in the presence of D-amino acid oxidase (DAAO), dehydrogenase, hydrogen donor, oxidized coenzyme NADP+, L-glutamate dehydrogenase mutant and an inorganic amino donor.

When the reduction reaction, the oxidation reaction, and the amination reaction are performed simultaneously, the NADPH used in the amination reaction can be generated cyclically by the reduction reaction. The oxidized coenzyme NADP$^+$ can be of conventional concentration in the art, and in order to ensure that the reaction can be conducted normally, the mass ratio of the oxidized coenzyme NADP$^+$ to the 2-oxo-4-(hydroxymethylphosphinyl) butyrate is 1:100-1:20000, preferably 1: 1000-1:15000, more preferably 1:5000.

The reaction time of the method is as follows: the reaction can be stopped when a desired final concentration of the raw materials, or a desired final concentration of products, or a desired conversion rate of products be achieved under the condition of detection by a conventional method which comprises a pre-column derivatization of high-performance liquid phase chromatography or an ion-pair chromatography, etc.

The sixth technical solution that solves the above-mentioned technical problems in the present invention is provided as follows: a method for preparing an L-glufosinate, wherein the method comprises the following steps:

(1) preparing an L-glufosinate salt according to the method described above;
(2) subjecting the L-glufosinate prepared in step (1) to an acidification reaction to obtain an L-glufosinate.

The seventh technical solution that solves the above-mentioned technical problems in the present invention is provided as follows: a use of the L-glutamate dehydrogenase mutant prepared above in the preparation of an L-glufosinate or salts thereof.

The use can comprise the following steps: 2-oxo-4-(hydroxymethylphosphinyl) butyrate is subjected to a reaction in the presence of an L-amino acid dehydrogenase, an inorganic amino donor and a reduced coenzyme to obtain an L-glufosinate.

Or, the use can comprise the following steps: 2-oxo-4-(hydroxymethylphosphinyl) butyric acid is subjected to a reaction to obtain an L-glufosinate in the presence of an L-amino acid dehydrogenase, an inorganic amino donor and a reduced coenzyme.

Or, the use can comprise the following steps: 2-oxo-4-(hydroxymethylphosphinyl) butyrate is subjected to a reaction to obtain an L-glufosinate salt in the presence of an L-amino acid dehydrogenase, an inorganic amino donor and a reduced coenzyme, then subjected to an acidification reaction.

In the present invention, the L-glufosinate salt can exist in the form of L-glufosinate ammonium salt.

Unless otherwise specified, the concentrations of the above compounds are the concentration of the compound in an entire reaction system before a reaction.

On the basis of conforming to common knowledge in the field, the above-mentioned preferred conditions can be combined arbitrarily to obtain preferred embodiments of the present invention.

The reagents and raw materials used in the present invention are all commercially available.

The positive and progressive effects of the present invention are:

Compared to the L-glutamate dehydrogenase mutant with mutating at single position (position 175 or 386), the present L-glutamate dehydrogenase mutant has a higher specific activity of enzyme when preparing an L-glufosinate or salts thereof, thereby increasing the efficiency (such as higher conversion rate when participating in a reaction, stronger stereoselectivity) of the action of the enzyme and reducing reaction costs, which are beneficial to industrial production.

DETAILED DESCRIPTION OF THE INVENTION

Figure 1:
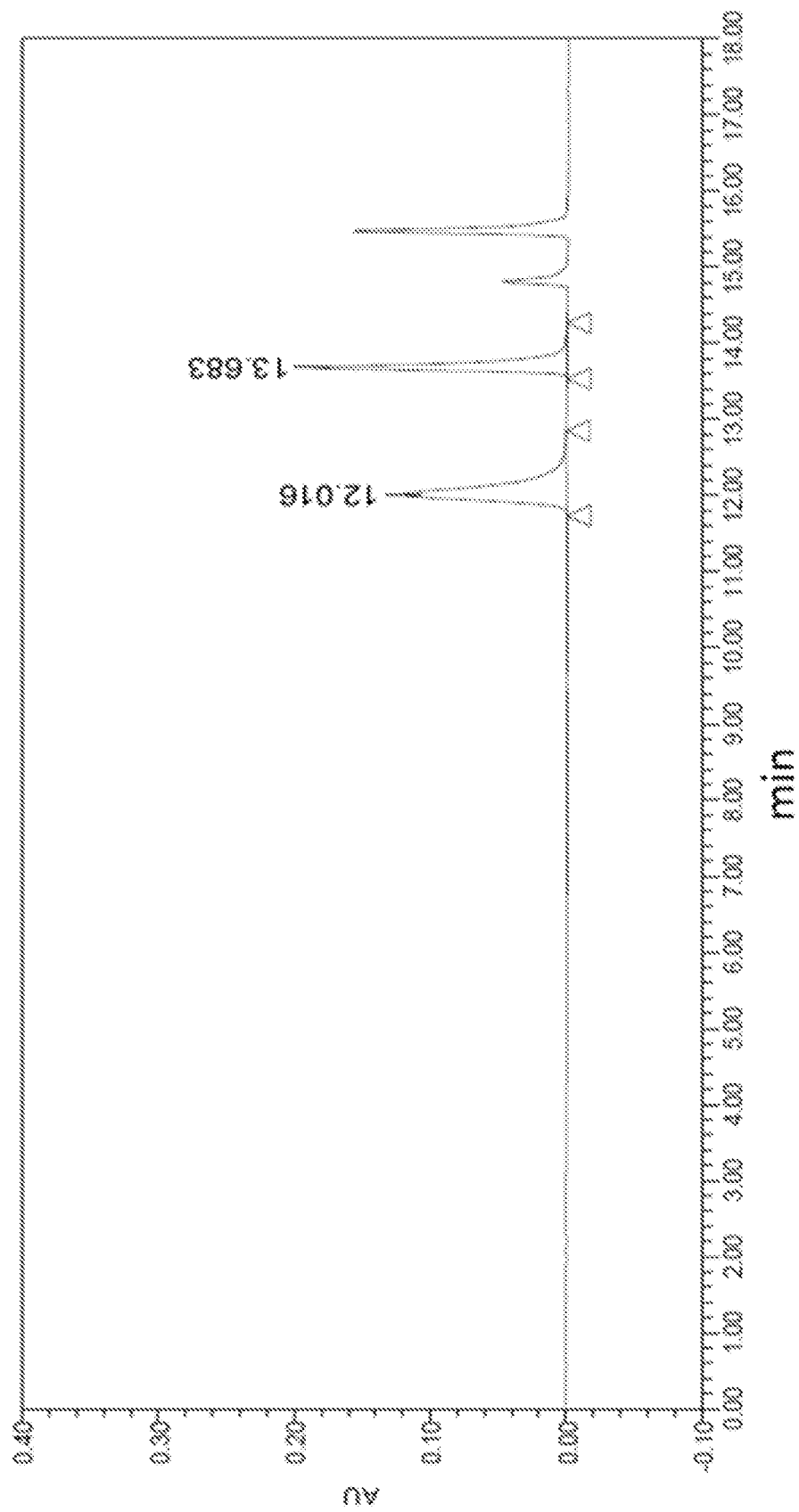
FIG. 1 shows Marfey's reagent pre-column derivatization HPLC analysis result of racemic glufosinate standard, wherein the last two peaks are the peaks of the Marfey's reagent itself.

The present invention will be further illustrated by the following examples, but the present invention is not limited to the scope of examples thereto. The experimental methods for which specific conditions are not indicated in the following examples shall be selected according to conventional methods and conditions, or according to the specification of commodity.

Unless otherwise specified, the experimental methods of the present invention are conventional methods, and specific gene cloning operations can be found in the "Molecular Cloning: A Laboratory Manual" compiled by J. Sambrook et al.

Unless otherwise specified, the abbreviations of amino acids in the present invention are conventional in the art, and the amino acids corresponding to the specific abbreviations are shown in Table 1.

TABLE 1

| Name of Amino Acid | Three-Letter Code | Single Letter Code |
|---|---|---|
| alanine | Ala | A |
| arginine | Arg | R |
| asparagine | Asn | N |
| aspartic acid | Asp | D |
| cysteine | Cys | C |
| glutanine | Gln | Q |
| glutamic acid | Glu | E |
| glycine | Gly | G |
| histidine | His | H |
| isoleucine | Ile | I |
| leucine | Leu | L |
| lysine | Lys | K |
| methionine | Met | M |
| phenylalanine | Phe | F |
| proline | Pro | P |
| serine | Ser | S |
| threonine | Thr | T |
| tryptophan | Trp | W |
| tyrosine | Tyr | Y |
| valine | Val | V |

The codons corresponding to the amino acids are also conventional in the art, and the corresponding relationships between specific amino acids and codons are shown in Table 2.

TABLE 2

| First Nucleotide | Second Nucleotide | | | | Third Nucleotide |
|---|---|---|---|---|---|
| | T | C | A | G | |
| T | F(Phenylalanine) | S(Serine) | Y(Tyrosine) | C(Cysteine) | T |
| | F(Phenylalanine) | S(Serine) | Y(Tyrosine) | C(Cysteine) | C |
| | L(Leucine) | S(Serine) | Stop Codon | Stop Codon | A |
| | L(Leucine) | S(Serine) | Stop Codon | W(Tryptophan) | G |
| C | L(Leucine) | P(Proline) | H(Histidine) | R(Arginine) | T |
| | L(Leucine) | P(Proline) | H(Histidine) | R(Arginine) | C |
| | L(Leucine) | P(Proline) | Q(Glutamine) | R(Arginine) | A |
| | L(Leucine) | P(Proline) | Q(Glutamine) | R(Arginine) | G |
| A | I(Isoleucine) | T(Threonine) | N(Asparagine) | S(Serine) | T |
| | I(Isoleucine) | T(Threonine) | N(Asparagine) | S(Serine) | C |
| | I(Isoleucine) | T(Threonine) | K(Lysine) | R(Arginine) | A |
| | M(Methionine) | T(Threonine) | K(Lysine) | R(Arginine) | G |
| G | V(Valine) | A(Alanine) | D(Aspartic acid) | G(Glycine) | T |
| | V(Valine) | A(Alanine) | D(Aspartic acid) | G(Glycine) | C |
| | V(Valine) | A(Alanine) | E(Glutamate) | G(Glycine) | A |
| | V(Valine) | A(Alanine) | E(Glutamate) | G(Glycine) | G | pET28a was purchased from Novagen; NdeI and HindIII were purchased from Thermo Fisher, and *E. coli* BL21 (DE3) competent cells were purchased From Beijing Dingguo Changsheng Biotechnology Co., Ltd.; the catalase was purchased from Shandong Fengtai Biotechnology Co., Ltd.; NADPH was purchased from Shenzhen Bontac Bio-engineering Co., Ltd.; $NH_4Cl$ was purchased from Shanghai Titan Technology Co., Ltd.

The chiral analysis of the product was performed by pre-column derivatization high performance liquid chromatography (HPLC), and the specific analysis method is as follows:

(1) Chromatographic conditions: Agilent ZORBAX Eclipse plus C18, 3.5 μm, 150*4.6 mm. Mobile phase A: 0.1% $TFA+H_2O$, mobile phase B: 0.1% TFA+CAN. Detection wavelength: 340 nm, flow rate: 1.0 mL/min, column temperature: 30° C.

(2) Derivatization reagent: Marfey's reagent. 50 mg of N-α-(2,4-dinitro-5-fluorophenyl)-L-alaninamide was weighed accurately, and dissolved with acetonitrile to prepare 25 mL solution for later use.

(3) Derivatization reaction: The reaction solution was diluted 100 times and added with equal volume of Marfey's reagent for derivatization. 10 μL of mixture was injected for analysis.

Conversion rate=(reactant−remaining reactant)/reactant×100%

2-oxo-4-(hydroxymethylphosphinyl) butyric acid (PPO for short) was analyzed by ion-pair high performance liquid chromatography (HPLC). The specific analysis method is as follows: Chromatographic conditions: ULtimate AQ-C18, 5 μm, 4.6*250 mm; mobile phase: 0.05 mol/L diammonium hydrogen phosphate PH=3.6: 10% tetrabutylammonium hydroxide aqueous solution: acetonitrile=91:1:8; detection wavelength: 205 nm; flow rate: 1.0 mL/min; column temperature: 25° C. In the following examples, the terms described are all "glufosinate", since "glufosinate" is in the reaction system, a person skilled in the art refer to "glufosinate ammonium salt" as "glufosinate" by default. Therefore, "glufosinate" refers to "glufosinate ammonium salt" actually, and the corresponding glufosinate standard also refer to glufosinate ammonium salt standard, and the corresponding PPO is also PPO ammonium salt. Before the optical rotation of glufosinate is tested, the resulting glufosinate ammonium salt is subjected to the acidification reaction to obtain glufosinate.

Example 1 Acquisition of Mutant Enzymes of L-Glutamate Dehydrogenase

The sequence of a glutamate dehydrogenase (referred to as LsGluDH for short hereinafter) derived from *Lysinibacillus sphaericus* was searched out on NCBI, shown as SEQ ID NO: 1, with Genbank Accession No.: WP_012293812.1. Genes were synthesized according to the nucleotide sequences of the genes of mutants as SEQ ID NO: 4, SEQ ID NO: 6, SEQ ID NO: 8 and SEQ ID NO: 10 in Table 3, and the genes were synthesized by Suzhou Genewiz Biotechnology Co., Ltd. (Building C3, Bionano Technology Park, Xinghu Street 218, Suzhou Industrial Park).

Then, the genes of mutants were enzyme-ligated to pET28a with NdeI and HindIII as restriction sites. The vector enzyme-ligated was transformed into *E. coli* BL21 competent cells. The constructed bacterial seed was inoculated on TB medium at 37° C., shaking with 200 rpm, and induced with 0.1 mM IPTG overnight. The bacteria was then harvested, and the engineered bacteria containing the gene of glutamate dehydrogenase were obtained.

After the engineered bacteria containing the gene of glutamate dehydrogenase were activated by plate-streaking, single colony was selected and inoculated into 5 mL LB liquid medium containing 50 μg/mL kanamycin, and cultured with shaking at 37° C. for 12 h. 2% of inoculum was transferred to 50 mL fresh LB liquid medium containing 50 μg/mL kanamycin the same, shook at 37° C. until OD600 value reached about 0.8. IPTG was added to a final concentration of 0.5 mM for induced culturing at 18° C. for 16 h. After cultivation, the culture solution was centrifuged at 10,000 rpm for 10 min, the supernatant was discarded, and the bacteria was collected and stored in an ultra-low temperature refrigerator at −80° C. for later use.

5 g of bacteria collected above was washed twice with 50 mM Tris-HCl buffer solution, pH 8.5, resuspended in 30 mL of Tris-HCl buffer solution with pH 8.5, and lysed homogeneously. The lysis liquid was centrifuged at 12,000 rpm for 10 min to remove precipitation, and a supernatant crude enzyme solution containing a recombinant glutamate dehydrogenase was obtained.

TABLE 3

| Mutant No. | Mutation Site | SEQ ID NO. of amino acid sequences | SEQ ID NO. of nucleotide sequences |
|---|---|---|---|
| 1 | LsGluDH-WT (WP_012293812.1) | 1 | 2 |
| 1-1 | LsGluDH-A175G | 3 | 4 |
| 1-2 | LsGluDH-V386A | 5 | 6 |
| 1-3 | LsGluDH-A175G-V386S | 7 | 8 |
| 1-4 | LsGluDH-A175G-V386A | 9 | 10 |

Example 2 Test of Specific Activity of Enzyme on Mutant Enzymes

Figure 6:
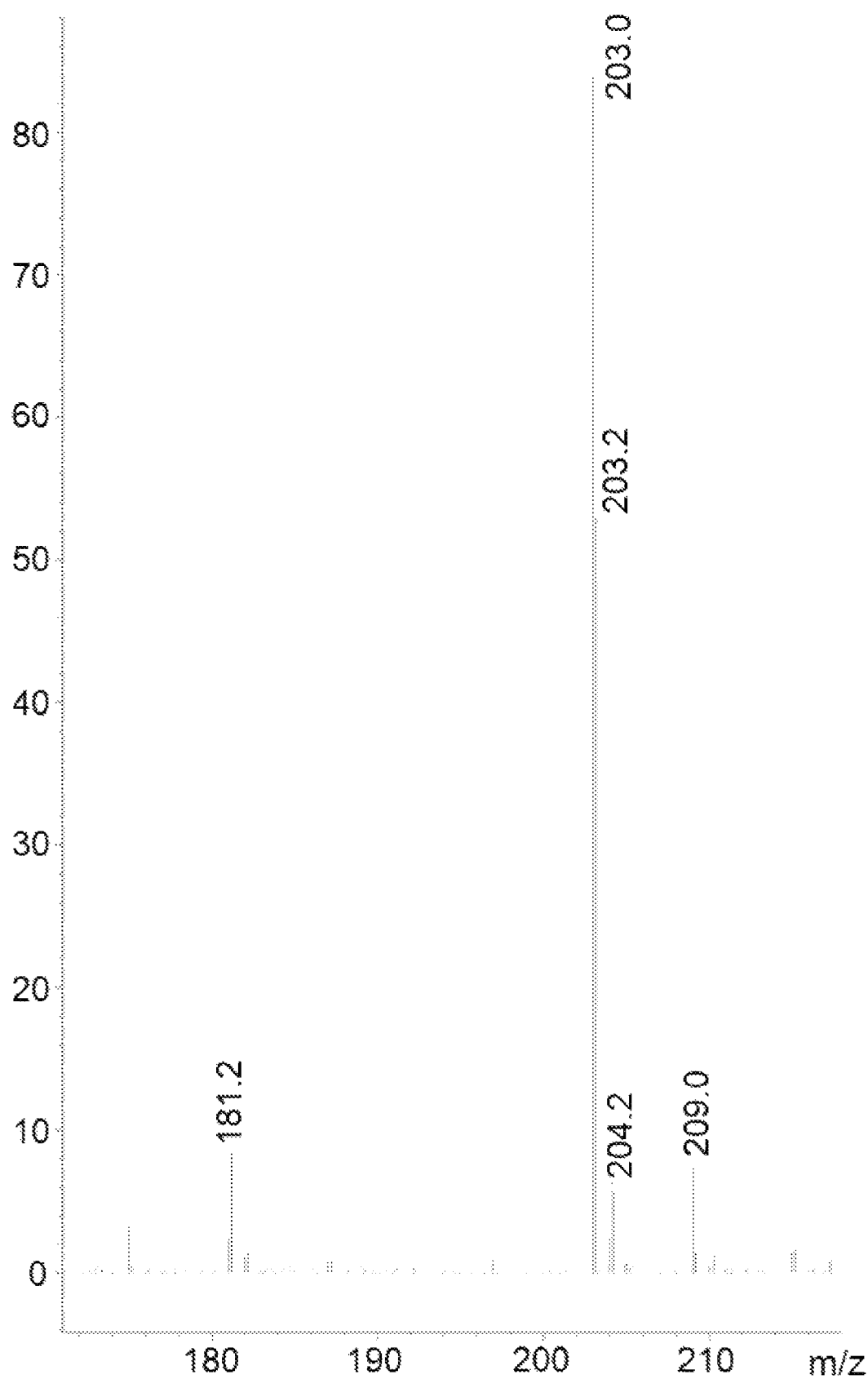
FIG. 6 shows mass spectrum of PPO standard.

The substrate solution is prepared as: 355 μL of 2.25 M PPO (in a final concentration of 20 mM) (prepared by inventors, and the method for preparation was referred to U.S. Pat. No. 8,017,797B, FIG. 6 is the corresponding mass spectrum) and 0.4 g of $NH_4Cl$ (in a final concentration of 200 mM) were added. The pH was adjusted by ammonia to 8.5, and the volume was made constant to 40 mL by 50 mM Tris-HCl buffer solution of pH 8.5.

The method for testing enzyme activity is as follows:

The total reaction system is 1 mL, and absorbance value was measured at OD340 nm. 940 μL of the substrate solution was added to a cuvette of 1 mL, and the value was adjusted to zero; then 10 μL of 25 mM NADPH was added; finally 50 μL of the crude enzyme solution was added in order. The value changes in 0-10 min were recorded, then one value was picked every 30 s, and a plot was made with the reaction time as abscissa and the absorbance value at 340 nm of wavelength as Y-axis. The slope was used to calculate the reducing rate of NADPH, and the enzyme activity was calculated.

The unit of enzyme activity is defined as the amount of enzyme required to reduce 1 μmol of NADPH per minute under specific reaction conditions (30° C.).

The specific activity of enzyme is the activity units contained in per mg of enzyme protein, and the calculation formula is: enzyme activity/protein content, the unit of which is U/mg or U/g. The results are shown in Table 4.

It is known in CN108588045A that the enzyme activity of wildtype LsGluDH-WT (WP_012293812.1) is much lower than that of single-position mutant, and a person skilled in the art can figure out that the specific activity of enzyme of wildtype LsGluDH-WT (WP_012293812.1) is much lower than that of mutants. Therefore, the specific activity of enzyme of wildtype LsGluDH-WT (WP_012293812.1) was not tested in the present invention.

TABLE 4

| Mutant No. | Mutation Site | Specific activity of enzyme (U/g) | SEQ ID NO. of amino acid sequences | SEQ ID NO. of nucleotide sequences |
|---|---|---|---|---|
| 1-1 | LsGluDH-A175G | 38.19 | 3 | 4 |
| 1-2 | LsGluDH-V386A | 26.64 | 5 | 6 |
| 1-3 | LsGluDH-A175G-V386S | 49.44 | 7 | 8 |
| 1-4 | LsGluDH-A175G-V386A | 58.73 | 9 | 10 |

Methods for preparing the crude enzyme solution of L-glutamate dehydrogenase used in the following examples are all as described above.

Example 3 Acquisition of D Amino Add Oxidase (DAAO) Gene

The whole gene of DAAO was synthesized according to the gene sequence of AC302 DAAO described in U.S. Pat. No. 9,834,802B2. Synthesis was conducted by Suzhou Genewiz Biological Technology Co., Ltd., No. 211 Pubin Road, R & D Park, Jiangbei New District, Nanjing, Jiangsu Province.

Example 4 Expression of D Amino Acid Oxidase (DAAO) Gene

The composition of LB liquid medium is as follows: peptone 10 g/L, yeast powder 5 g/L, NaCl 10 g/L, after dissolving them in deionized water and calibrated to a constant volume, LB liquid medium was sterilized at 121° C. for 20 min for later use.

DAAO gene synthesized in Example 3 was ligated to pET28a, with restriction sites NdeI & HindIII, and the ligated vector was transformed into host E. coli BL21 (DE3) competent cells to obtain engineered strains containing DAAO.

After activating the engineered strain containing DAAO gene by plate-streaking, a single colony was selected and inoculated into 5 mL of LB liquid medium containing 50 μg/mL kanamycin, and cultured with shaking at 37° C. for 12 h. 2% of inoculum was transferred to 50 mL of fresh LB liquid medium containing 50 μg/mL kanamycin, shook at 37° C. until the $OD_{600}$ value reached about 0.8. IPTG was added to a final concentration of 0.5 mM for induced culturing at 18° C. for 16 h. After cultivation, the culture solution was centrifuged at 10,000 rpm for 10 min, the supernatant was discarded, and the bacteria was collected and stored in an ultra-low temperature refrigerator at −20° C. for later use.

Example 5 Preparation of D Amino Acid Oxidase (DAAO) Crude Enzyme Solution and Enzyme Activity Detection After cultivation, the collected bacteria in Example 4 was washed twice with 50 mM phosphate buffer solution, pH 8.0, resuspended in phosphate buffer solution with pH 8.0, and lysed homogeneously at low temperature and high pressure. The lysis liquid was centrifuged to remove cell pellets, thus obtaining supernatant as a crude enzyme solution containing recombinant DAAO.

The detection method of enzyme activity is as follows: 100 μL of pH 8.0 disodium hydrogen phosphate-sodium dihydrogen phosphate buffer (containing 50 mmol/L of D-glufosinate and 0.1 mg/mL of peroxidase), 50 μL of indicator (60 μg/mL of 2,4,6-tribromo-3-hydroxybenzoic acid and 1 mg/mL of 4-aminoantipyrine), 50 μL of DAAO enzyme were added, the concentration of $H_2O_2$ was determined by detecting UV absorption at 510 nm, the concentration of PPO was calculated and the enzyme activity was obtained.

The unit of enzyme activity is defined as the amount of enzyme required to produce 1 μmol of PPO per minute under specific reaction conditions (30° C.).

Methods for preparing the crude enzyme solution of DAAO enzyme used in the following examples are all as described above.

Example 6 Acquisition and Expression of Alcohol Dehydrogenase Gene

The whole gene of alcohol dehydrogenase was synthesized according to the gene sequence of Cyclopentanol dehydrogenase from Lactobacillus brevis KB290 (Genbank Accession No.: BAN05992.1).

The composition of LB liquid medium consists of: peptone 10 g/L, yeast powder 5 g/L, NaCl 10 g/L, after dissolving them in deionized water, make the volume constant, and sterilized at 121° C. for 20 min for later use.

The alcohol dehydrogenase gene was ligated to pET28a, with restriction sites NdeI & HindIII, and the ligated vector was transformed into host E. coli BL21 (DE3) competent cells to obtain engineered strains containing the alcohol dehydrogenase gene. After activating the engineered strains containing the alcohol dehydrogenase gene by plate-streaking, a single colony was selected and inoculated into 5 mL of LB liquid medium containing 50 μg/mL kanamycin, and cultured with shaking at 37° C. for 12 h. 2% of inoculum was transferred to 50 mL of fresh LB liquid medium containing 50 μg/mL kanamycin the same, shook at 37° C. until the $OD_{600}$ value reached about 0.8. IPTG was added to a final concentration of 0.5 mM for induced culturing at 18° C. for 16 h. After cultivation, the culture solution was centrifuged at 10,000 rpm for 10 min, the supernatant was discarded, and the bacteria was collected and stored in an ultra-low temperature refrigerator at −20° C. for later use.

Example 7 Preparation of Crude Alcohol Dehydrogenase Solution and Measurement of Enzyme Activity 10 g of bacterial sludge was taken from the collected bacteria in Example 6 and added with 50 mL of 100 mM ammonium phosphate buffer solution with pH 7.5. The mixture was stirred well, and lysed homogeneously at 500 bar as crude enzyme solution. 10% flocculant was added dropwise under the condition of stirring (in a final concentration of 2-2.5‰), centrifuged at 4,000 rpm for 10 min after stirred for 5 minutes to obtain clear enzyme solution. The enzyme activity of the supernatant was measured.

The method for detecting enzyme activity is as follows: in a 3 mL of reaction system and under the condition of 25° C., first, a 2850 μL of 400 mM isopropanol (prepared with 100 mM phosphate buffer) with pH 8.0 was added first, then 50 μL of NADP$^+$(25 mM) was added. After adjusting the UV spectrophotometry meter to zero, then 100 μL of enzyme solution diluted 100 folds was added, and OD value at 340 nm was measured by an ultraviolet spectrophotometer.

The unit of enzyme activity is defined as follows: the amount of enzyme required to produce 1 μmol of NADPH per minute under specific reaction conditions (25° C., pH 7.0) is defined as 1 U.

Methods for preparing the crude enzyme solution of glucose dehydrogenase used in the following examples are all as described above.

Example 8 Preparation of L-Glufosinate Catalysed by DAAO Enzyme and L-Glutamate Dehydrogenase Mutant 200 g of bacteria of L-glutamate dehydrogenase mutant (prepared according to Example 1) was resuspended by 50 mM phosphate buffer solution with pH 8.0, and the volume was made constant to 1 L. The solution was lysed homogeneously at low temperature and high pressure. The lysis liquid was centrifuged to remove precipitation, thus obtaining the crude enzyme solution containing L-glutamate dehydrogenase mutant.

80 g of D, L-glufosinate was weighed and dissolved completely with 50 mM of disodium hydrogen phosphate-sodium dihydrogen phosphate buffer with pH 8.0. 2.5 g of 0.4 million U/g catalase was added, and 150 mL of the crude enzyme solution of DAAO enzyme (12 U/mL) prepared by Example 5 was added. The pH was adjusted to 8.0 by ammonia, and the volume was made constant to 1 L by 50 mM disodium hydrogen phosphate-sodium dihydrogen phosphate buffer. The reaction was conducted in water bath using mechanical stirring at 20° C., and under the condition of ventilation by introducing air at 1 VVM (introduce one-fold of reaction volume of air per minute). 1 mL of defoamer was added to avoid foaming, and the production concentration of PPO was determined by ion-pair HPLC. Meanwhile the content and ee value of remaining L-glufosinate were determined by pre-column derivatization high performance liquid chromatography. When the ee value was greater than 99%, the reaction was stopped. At this time, more than 99% of the D-glufosinate was reacted to producing PPO, wherein the residual amount of the D-glufosinate accounts for less than 1% of the initial amount of the D-glufosinate, accounts for less than 0.5% of the initial amount of the D, L-glufosinate. In the reaction solution, PPO is more than 49.5% (in mole) of the total amount of PPO, L-glufosinate and D-glufosinate; D-glufosinate is less than 0.5% (in mole) of the total amount of PPO, L-glufosinate and D-glufosinate; L-glufosinate is 50% (in mole) of the total amount of PPO, L-glufosinate and D-glufosinate, which is equal to the initial proportion of L-glufosinate in D, L-glufosinate.

Four aliquots of 50 mL of the reaction solution above were added with 0.54 g of ammonium chloride, 0.4 mg of NADP+ and 0.73 g of isopropanol respectively. 1 mL of alcohol dehydrogenase (300 U/mL) prepared in Example 7 was added, and 1 mL of the crude enzyme solution of L-glutamate dehydrogenase mutant was added respectively. The pH was adjusted by ammonia to 8.5, and the reaction temperature was controlled at 37° C. by performing reaction in water bath and magnetically stirred. The residual concentration of PPO was determined by ion-pair HPLC, and meanwhile the content and ee value of L-glufosinate were determined by pre-column derivatization high performance liquid chromatography. The date at the end of the reaction is shown in Table 5.

Figure 2:
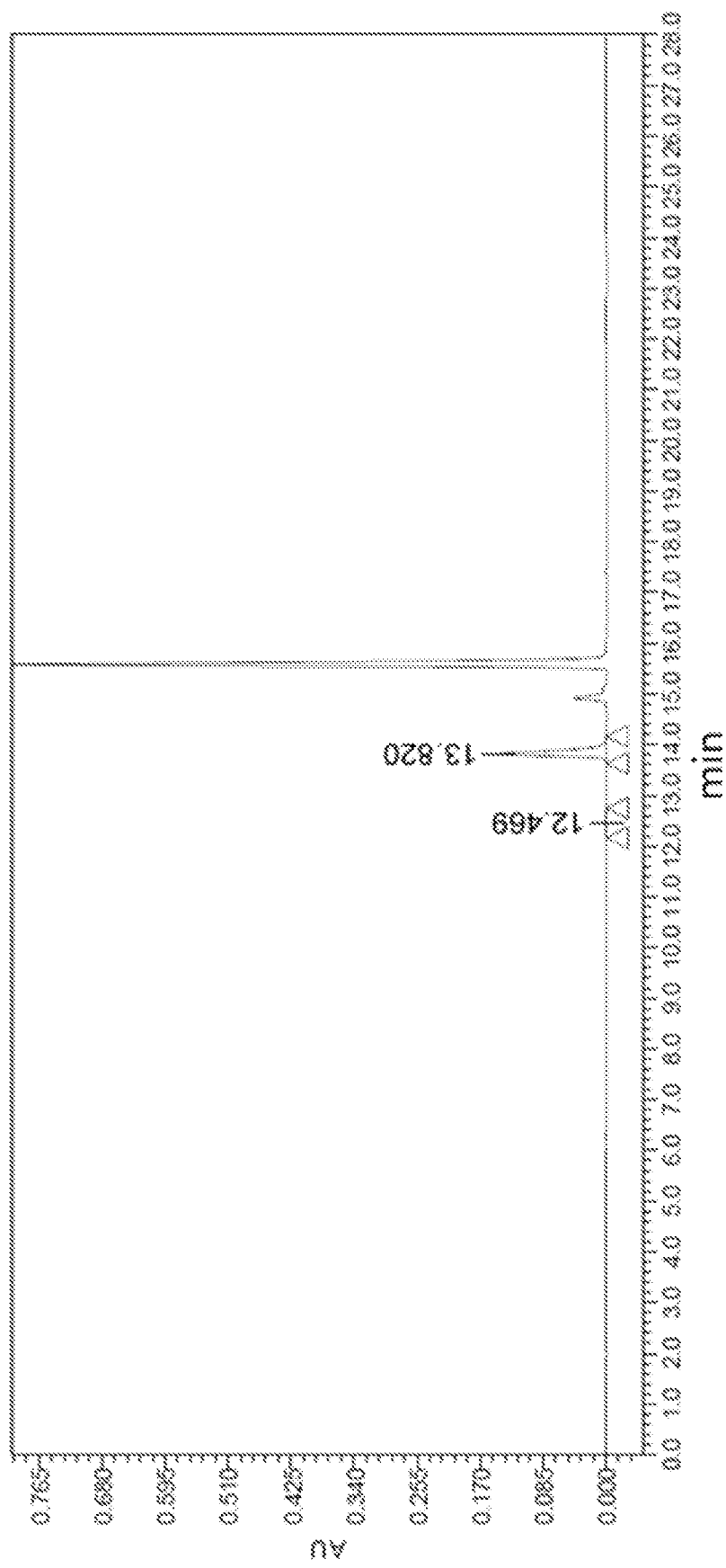
FIG. 2 shows Marfey's reagent pre-column derivatization HPLC analysis result of the D-glufosinate and the L-glufosinate in the prepared product.

The HPLC analysis results of D-glufosinate and L-glufosinate in the products after reaction completion (18 h) are shown in FIG. 2 (in the drawings, L-glutamate dehydrogenase mutant 1-4 (LsGluDH-A166G-V376A) is used as an example for illustration), wherein L-glufosinate has the retention time of 13.820 min, and D-glufosinate with the retention time of 12.469 min is almost undetectable; the HPLC chromatogram of Marfey's reagent pre-column derivatization of the racemic glufosinate standard (purchased from Shanghai Aladdin Biochemical Technology Co., Ltd.) is shown in FIG. 1 (the retention time of L-glufosinate and D-glufosinate are 13.683 min and 12.016 min, respectively). The peak time of the composition of the product prepared in this example is generally the same with that of the L-glufosinate in the standard product. In addition, it is indicated that L-glufosinate was prepared in present example by conducting acidification treatment, concentration, purification by column, recrystallization on products obtained, to obtain pure L-glufosinate, which has $[\alpha]D^{25}$=+28.2° (C=1,1N HCl) determined by optical rotation (the optical rotation of L-glufosinate has been reported in prior art, such as U.S. Pat. No. 4,389,488).

Figure 3:
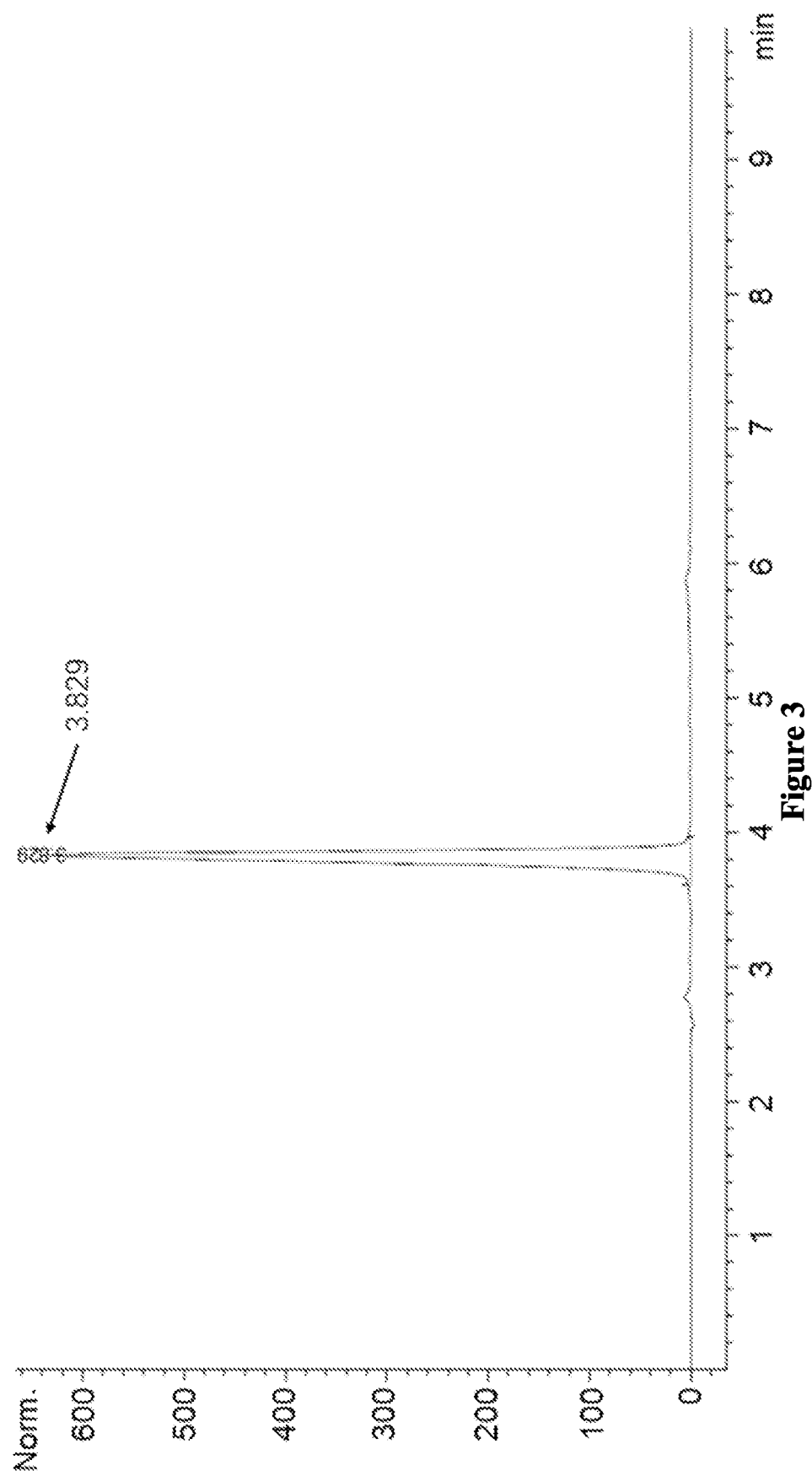
FIG. 3 shows ion-pair HPLC analysis result of racemic glufosinate standard.
Figure 4:
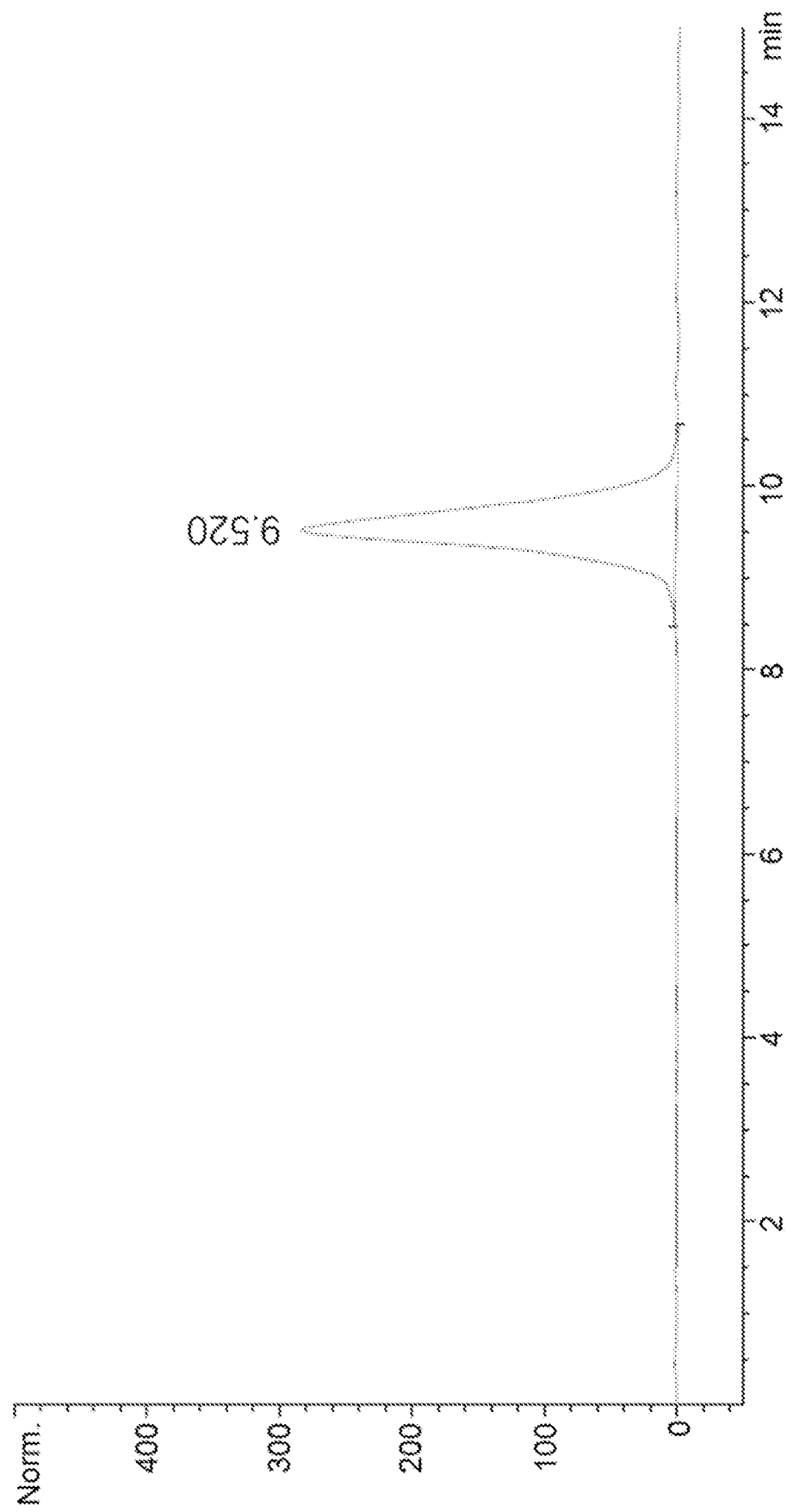
FIG. 4 shows ion-pair HPLC analysis result of PPO standard.
Figure 5:
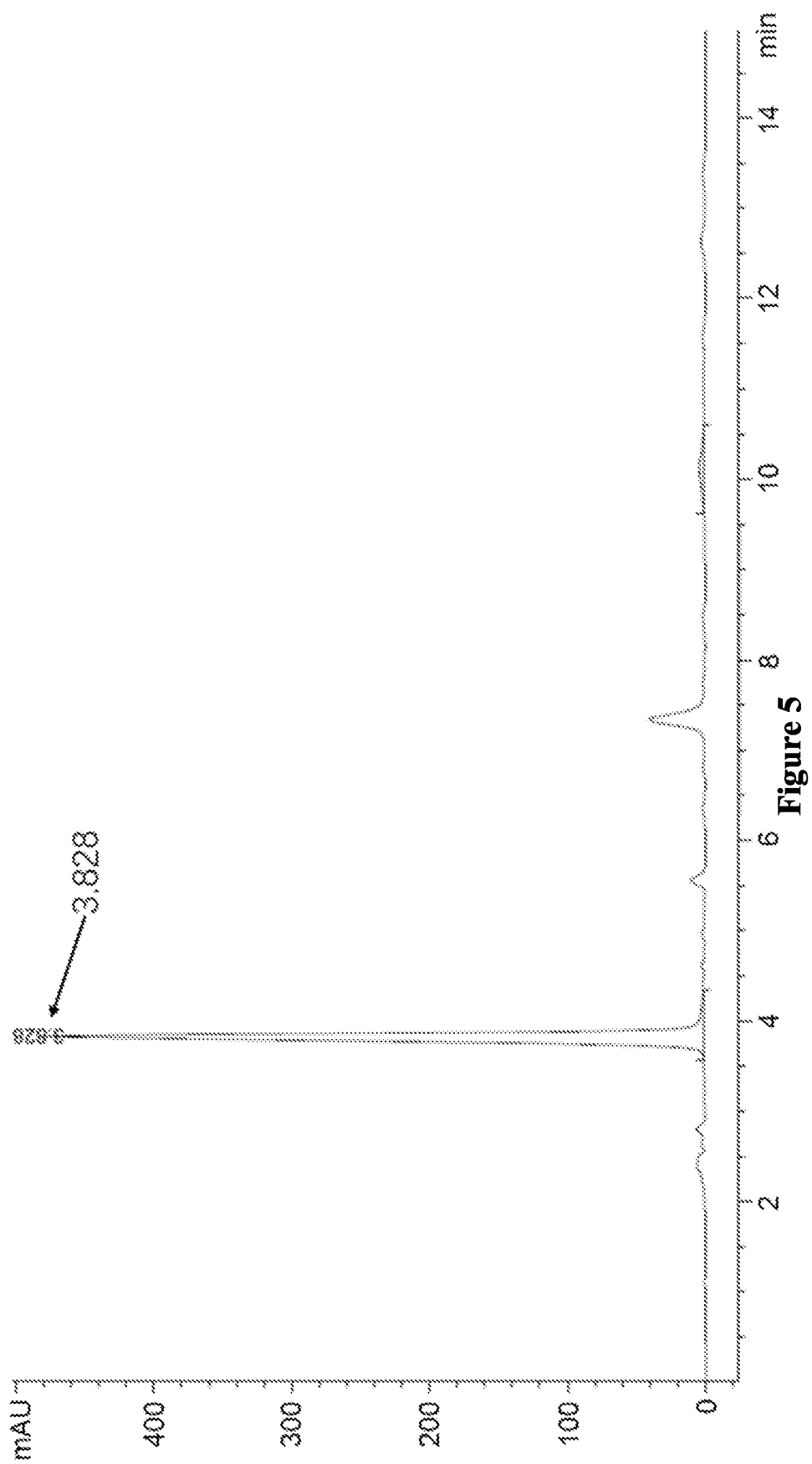
FIG. 5 shows ion-pair HPLC analysis result of reaction mixture after reaction.

The ion-pair HPLC analysis results of the reaction solution after reaction completion (18 h) are shown in FIG. 5, wherein no peak at the peak position of PPO, and 3.828 min is the peak position of glufosinate. The ion-pair HPLC spectrum of the PPO standard product (the standard product was prepared by inventors self, and the method for preparing was referred to U.S. Pat. No. 8,017,797B, FIG. 6 is the corresponding mass spectrum) is shown in FIG. 4, wherein the retention time of PPO standard product is 9.520 min. The ion-pair HPLC spectrum of the racemic glufosinate standard (purchased from Shanghai Aladdin Biochemical Technology Co., Ltd.) is shown in FIG. 3, wherein the retention time of racemic glufosinate standard is 3.829 min. It can be seen that PPO was completely reacted to conversion finally, and the peak time of glufosinate product is generally consistent with the peak time of the standard product.

Although L-glutamate dehydrogenase mutant 1-4 (LsGluDH-A166G-V376A) is taken as example in the above figure results, experiments on all other mutants were conducted by inventors to verify that the substrate can by catalyzed by these mutants in the present invention when participating in above reaction, thereby producing correct products.

TABLE 5

| Mutant No. | Mutation Site | Conversion rate at 2 h | Conversion rate at 18 h | ee value at 18 h |
|---|---|---|---|---|
| 1-1 | LsGluDH-A175G | 59.8% | >99% | >99% |
| 1-2 | LsGluDH-V386A | 62.9% | >99% | >99% |
| 1-3 | LsGluDH-A175G-V386S | 70.1% | >99% | >99% |
| 1-4 | LsGluDH-A175G-V386A | 76.1% | >99% | >99% |

Compare Example

A mutant enzyme of glutamate dehydrogenase derived from *Pseudomonas putida* (Genbank Accession No.: NP_742836.1) disclosed in CN108588045A (referred to as PpGluDH hereinafter) was obtained by performing the same method with that in Example 1, and the specific activity of enzyme was tested by the same method described in Example 2, and the results are shown in Table 6:

TABLE 6

| Mutant No. | Mutation Site | Specific activity of enzyme (U/g) | SEQ ID NO. of amino acid sequence | SEQ ID NO. of nucleotide sequence |
|---|---|---|---|---|
| 1' | PpGluDH-WT (NP_742836.1) | N.D. | 11 | 12 |
| 1'-1 | PpGluDH-A167G | 15.25 | 13 | 14 |
| 1'-2 | PpGluDH-V378A | 27.73 | 15 | 16 |
| 1'-4 | PpGluDH-A167G-V378A | 16.84 | 17 | 18 |

It can be seen in Table 6 that, the specific activity of enzyme mutants mutating at homologous sites of glutamate dehydrogenase derived from *Pseudomonas putida* is significantly lower than the mutants obtained in the present invention, and therefore, not all mutants with mutation at two sites have better effects than mutant with mutation at single site.

What is claimed is:

1. An L-glutamate dehydrogenase mutant, wherein the amino acid sequence of the L-glutamate dehydrogenase mutant is set forth in SEQ ID NO: 7 or SEQ ID NO: 9.

2. A method for preparing the L-glufosinate salt, comprising: subjecting 2-oxo-4-(hydroxymethylphosphinyl) butyrate to an amination reaction to obtain an L-glufosinate salt in the presence of a reaction solvent, an L-glutamate dehydrogenase mutant, an inorganic amino donor and a reduced coenzyme NADPH; wherein the L-glutamate dehydrogenase mutant is the L-glutamate dehydrogenase mutant of claim 1.

3. The method of claim 2, further comprising: subjecting a D-glufosinate salt to an oxidation reaction to obtain the 2-oxo-4-(hydroxymethylphosphinyl) butyrate in the presence of D-amino acid oxidase.

4. The method of claim 2, wherein the L-glutamate dehydrogenase mutant has a concentration of 0.05-3 U/m; and/or, the inorganic amino donor has a concentration of 100-2000 mM; and/or, the 2-oxo-4-(hydroxymethylphosphinyl) butyrate has a concentration of 100-600 mM; and/or, the mass ratio of the reduced coenzyme NADPH to the 2-oxo-4-(hydroxymethylphosphinyl) butyrate is 1:100-1:20000;

and/or, the inorganic amino donor is one or more of ammonia, ammonium sulfate, ammonium chloride, diammonium hydrogen phosphate, ammonium acetate, ammonium formate and ammonium bicarbonate;

and/or, the reaction solvent is water;

and/or, the amination reaction has a reaction system with a pH of 7-9;

and/or, the amination reaction has a reaction system with a temperature of 20-50° C.

5. The method of claim 2, further comprising: subjecting an oxidized coenzyme NADP$^+$ to a reduction reaction to obtain the reduced coenzyme NADPH in the presence of a dehydrogenase and a hydrogen donor.

6. A method for preparing an L-glufosinate, comprising:
(a) preparing an L-glufosinate salt according to the method of claim 2; and
(b) subjecting the L-glufosinate prepared in step (a) to an acidification reaction to obtain an L-glufosinate.

7. A method for preparing an L-glufosinate salt, comprising:
(a) subjecting a D-glufosinate salt is subjected to an oxidation reaction to obtain the 2-oxo-4-(hydroxymethylphosphinyl) butyrate in the presence of a D-amino acid oxidase; and (b) subjecting 2-oxo-4-(hydroxymethylphosphinyl) butyrate of step (a) to an amination reaction to obtain an L-glufosinate salt in the presence of a reaction solvent, an L-glutamate dehydrogenase mutant of claim 2, an inorganic amino donor and a reduced coenzyme NADPH.

8. The method of claim 7, wherein the D-glufosinate salt has a form of existing alone, or, coexisting with L-glufosinate salt; the form of coexisting with L-glufosinate salt is a D-type enriched glufosinate salt, an L-type enriched glufosinate salt or a racemic glufosinate salt.

9. The method of claim 3, wherein:
the D-glufosinate salt has a form of existing alone, or, coexisting with L-glufosinate salt; the form of coexisting with L-glufosinate salt is a D-type enriched glufosinate salt, an L-type enriched glufosinate salt or a racemic glufosinate salt;
and/or, the D-amino acid oxidase has a concentration of 0.6-6 U/mL;
and/or, the oxidation reaction is performed under a condition of ventilation;
and/or, the oxidation reaction is performed in the presence of catalase;
and/or, the D-glufosinate salt has a concentration of 100-600 mM;
and/or, the oxidation reaction has a reaction system with a pH of 7-9;
and/or, the oxidation reaction has a reaction system with a temperature of 20-50° C.

10. The method of claim 5, wherein:
the dehydrogenase is a glucose dehydrogenase, alcohol dehydrogenase or formate dehydrogenase;
and/or, the hydrogen donor is a glucose, isopropanol or formate;
and/or, the dehydrogenase has a concentration of 0.6-6 U/mL;
and/or, the mass ratio of the oxidized coenzyme $NADP^+$ to the 2-oxo-4-(hydroxymethylphosphinyl) butyrate is 1:100-1:20000;
and/or, the hydrogen donor has a concentration of 100-1000 mM;
and/or, the reduction reaction has a reaction system with a pH of 7-9;
and/or, the reduction reaction has a reaction system with a temperature of 20-50° C.

* * * * *

SEQUENCE LISTING

<160> NUMBER OF SEQ ID NOS: 18

<210> SEQ ID NO 1
<211> LENGTH: 457
<212> TYPE: PRT
<213> ORGANISM: Lysinibacillus sphaericus

<400> SEQUENCE: 1

```
Met Thr Ile Thr Thr Val Ser Asn Glu Gln Leu Ala Lys Glu Tyr Val
1               5                   10                  15

Asp Gly Val Phe Glu Gln Leu Lys Gln Gln Asn Cys His Gln Ala Glu
            20                  25                  30

Phe Leu Gln Ala Ala Glu Glu Ile Phe Ile Ser Leu Val Pro Val Phe
        35                  40                  45

Val Gln His Pro Gly Tyr Ile Lys Ala Asn Ile Leu Ser Arg Ile Val
    50                  55                  60

Glu Pro Asp Arg Ile Ile Ser Phe Arg Val Ala Trp Gln Asp His
65                  70                  75                  80

Asn Gln Val Gln Val Asn Arg Gly Tyr Arg Val Gln Tyr Ser Asn Val
                85                  90                  95

Met Gly Pro Tyr Lys Gly Gly Leu Arg Phe His Pro Ser Val Asn Glu
            100                 105                 110

Ser Ile Ile Lys Phe Leu Gly Phe Glu Gln Ile Phe Lys Asn Ala Leu
        115                 120                 125

Thr Gly Gln Pro Ile Gly Gly Gly Lys Gly Gly Ser Asn Phe Asp Pro
    130                 135                 140

Lys Gly Lys Ser Asp Ser Glu Ile Met Arg Phe Cys Gln Ala Phe Met
145                 150                 155                 160

Thr Glu Leu Tyr Arg His Ile Gly Pro Asp Val Asp Val Pro Ala Gly
                165                 170                 175

Asp Ile Gly Val Gly Ala Arg Glu Val Gly Tyr Leu Trp Gly Gln Tyr
            180                 185                 190

Lys Arg Leu Thr Lys Ala Ser Glu Ser Gly Val Leu Thr Gly Lys Thr
        195                 200                 205

Pro Gly Tyr Gly Gly Ser Leu Ala Arg Lys Glu Ala Thr Gly Tyr Gly
    210                 215                 220

Thr Val Tyr Phe Val Asn Glu Met Leu Lys Asp Val Asn Asp Ser Phe
225                 230                 235                 240
```

-continued

```
Glu Gly Lys Thr Val Val Val Ser Gly Ser Gly Asn Val Ser Thr Tyr
                245                 250                 255

Ala Ile Glu Lys Ala Gln Gln Tyr Gly Ala Lys Val Val Ala Cys Ser
            260                 265                 270

Asp Ser Ser Gly Tyr Ile Tyr Asp Pro Glu Gly Leu Asp Leu Asp Val
        275                 280                 285

Ile Lys Glu Ile Lys Glu Val Lys Gly Asp Arg Ile Ser Thr Tyr Val
    290                 295                 300

Ser Tyr Arg Pro Asn Ala Thr Phe Thr Asn Gly Cys Thr Gly Ile Trp
305                 310                 315                 320

Thr Ile Pro Cys Asp Ile Ala Leu Pro Cys Ala Thr Gln Asn Glu Ile
                325                 330                 335

Asn Gly Glu Ser Ala Arg Thr Leu Ile Ser Asn Gly Val Lys Ala Ile
            340                 345                 350

Gly Glu Gly Ala Asn Met Pro Ser Asp Leu Glu Ala Ile Asn Glu Phe
        355                 360                 365

Leu Asn Ala Gly Val Leu Phe Gly Pro Ala Lys Ala Ala Asn Ala Gly
    370                 375                 380

Gly Val Ala Val Ser Ala Leu Glu Met Ala Gln Asp Ser Ser Arg Val
385                 390                 395                 400

Phe Trp Ser Phe Glu Glu Val Asp Ala Lys Leu His Gln Ile Met Lys
                405                 410                 415

Asp Ile Tyr Ser Asp Ser Lys Ala Ala Ala Glu Lys Tyr Gly Phe Pro
            420                 425                 430

Gly Asn Leu Val Met Gly Ala Asn Ile Ala Gly Phe Ile Lys Val Ala
        435                 440                 445

Asp Gly Met Leu Thr Glu Gly Ile Tyr
    450                 455
```

<210> SEQ ID NO 2
<211> LENGTH: 1371
<212> TYPE: DNA
<213> ORGANISM: Lysinibacillus sphaericus

<400> SEQUENCE: 2

```
atgaccatca ccaccgtttc taacgaacag ctggctaaag aatacgttga cggtgttttc     60
gaacagctga aacagcagaa ctgccaccag gctgaattcc tgcaggctgc tgaagaaatc    120
ttcatctctc tggttccggt tttcgttcag cacccggaat acatcaaagc taacatcctg    180
tctcgtatcg ttgaaccgga ccgtatcatc tctttccgtg ttgcttggca ggacgaccac    240
aaccaggttc aggttaaccg tggttaccgt gttcagtact ctaacgttat gggtccgtac    300
aaaggtggtc tgcgtttcca cccgtctgtt aacgaatcta tcatcaaatt cctgggtttc    360
gaacagatct tcaaaaacgc tctgaccggt cagccgatcg gtggtggtaa aggtggttct    420
aacttcgacc cgaaaggtaa atctgactct gaaatcatgc gtttctgcca ggctttcatg    480
accgaactgt accgtcacat cggtccggac gttgacgttc cggctggtga catcggtgtt    540
ggtgctcgtg aagttggtta cctgtggggt cagtacaaac gtctgaccaa agcttctgaa    600
tctggtgttc tgaccggtaa aaccccgggt tacggtggtt ctctggctcg taaagaagct    660
accggttacg gtaccgttta cttcgttaac gaaatgctga aagacgttaa cgactctttc    720
gaaggtaaaa ccgttgttgt ttctggttct ggtaacgttt ctacctacgc tatcgaaaaa    780
gctcagcagt acggtgctaa agttgttgct tgctctgact cttctggtta catctacgac    840
ccggaaggtc tggacctgga cgttatcaaa gaaatcaaag aagttaaagg tgaccgtatc    900
```

```
tctacctacg tttcttaccg tccgaacgct accttcacca acggttgcac cggtatctgg    960
accatcccgt gcgacatcgc tctgccgtgc gctacccaga acgaaatcaa cggtgaatct   1020
gctcgtaccc tgatctctaa cggtgttaaa gctatcggtg aaggtgctaa catgccgtct   1080
gacctggaag ctatcaacga attcctgaac gctggtgttc tgttcggtcc ggctaaagct   1140
gctaacgctg tggtgttgc tgtttctgct ctggaaatgg ctcaggactc ttctcgtgtt    1200
ttctggtctt tcgaagaagt tgacgctaaa ctgcaccaga tcatgaaaga catctactct   1260
gactctaaag ctgctgctga aaaatacggt ttcccgggta acctggttat gggtgctaac   1320
atcgctggtt tcatcaaagt tgctgacggt atgctgaccg aaggtatcta c            1371
```

<210> SEQ ID NO 3
<211> LENGTH: 457
<212> TYPE: PRT
<213> ORGANISM: Artificial Sequence
<220> FEATURE:
<223> OTHER INFORMATION: LsGluDH-A175G

<400> SEQUENCE: 3

```
Met Thr Ile Thr Thr Val Ser Asn Glu Gln Leu Ala Lys Glu Tyr Val
1               5                   10                  15

Asp Gly Val Phe Glu Gln Leu Lys Gln Gln Asn Cys His Gln Ala Glu
            20                  25                  30

Phe Leu Gln Ala Ala Glu Glu Ile Phe Ile Ser Leu Pro Val Pro Phe
        35                  40                  45

Val Gln His Pro Glu Tyr Ile Lys Ala Asn Ile Leu Ser Arg Ile Val
    50                  55                  60

Glu Pro Asp Arg Ile Ile Ser Phe Arg Val Ala Trp Gln Asp Asp His
65                  70                  75                  80

Asn Gln Val Gln Val Asn Arg Gly Tyr Arg Val Gln Tyr Ser Asn Val
                85                  90                  95

Met Gly Pro Tyr Lys Gly Gly Leu Arg Phe His Pro Ser Val Asn Glu
            100                 105                 110

Ser Ile Ile Lys Phe Leu Gly Phe Glu Gln Ile Phe Lys Asn Ala Leu
        115                 120                 125

Thr Gly Gln Pro Ile Gly Gly Lys Gly Gly Ser Asn Phe Asp Pro
    130                 135                 140

Lys Gly Lys Ser Asp Ser Glu Ile Met Arg Phe Cys Gln Ala Phe Met
145                 150                 155                 160

Thr Glu Leu Tyr Arg His Ile Gly Pro Asp Val Asp Val Pro Gly Gly
                165                 170                 175

Asp Ile Gly Val Gly Ala Arg Glu Val Gly Tyr Leu Trp Gly Gln Tyr
            180                 185                 190

Lys Arg Leu Thr Lys Ala Ser Glu Ser Gly Val Leu Thr Gly Lys Thr
        195                 200                 205

Pro Gly Tyr Gly Gly Ser Leu Ala Arg Lys Glu Ala Thr Gly Tyr Gly
    210                 215                 220

Thr Val Tyr Phe Val Asn Glu Met Leu Lys Asp Val Asn Asp Ser Phe
225                 230                 235                 240

Glu Gly Lys Thr Val Val Ser Gly Ser Gly Asn Val Ser Thr Tyr
                245                 250                 255

Ala Ile Glu Lys Ala Gln Gln Tyr Gly Ala Lys Val Val Ala Cys Ser
            260                 265                 270

Asp Ser Ser Gly Tyr Ile Tyr Asp Pro Glu Gly Leu Asp Leu Asp Val
```

```
                275                 280                 285
Ile Lys Glu Ile Lys Glu Val Lys Gly Asp Arg Ile Ser Thr Tyr Val
        290                 295                 300

Ser Tyr Arg Pro Asn Ala Thr Phe Thr Asn Gly Cys Thr Gly Ile Trp
305                 310                 315                 320

Thr Ile Pro Cys Asp Ile Ala Leu Pro Cys Ala Thr Gln Asn Glu Ile
                325                 330                 335

Asn Gly Glu Ser Ala Arg Thr Leu Ile Ser Asn Gly Val Lys Ala Ile
                340                 345                 350

Gly Glu Gly Ala Asn Met Pro Ser Asp Leu Glu Ala Ile Asn Glu Phe
                355                 360                 365

Leu Asn Ala Gly Val Leu Phe Gly Pro Ala Lys Ala Ala Asn Ala Gly
        370                 375                 380

Gly Val Ala Val Ser Ala Leu Glu Met Ala Gln Asp Ser Ser Arg Val
385                 390                 395                 400

Phe Trp Ser Phe Glu Glu Val Asp Ala Lys Leu His Gln Ile Met Lys
                405                 410                 415

Asp Ile Tyr Ser Asp Ser Lys Ala Ala Ala Glu Lys Tyr Gly Phe Pro
                420                 425                 430

Gly Asn Leu Val Met Gly Ala Asn Ile Ala Gly Phe Ile Lys Val Ala
            435                 440                 445

Asp Gly Met Leu Thr Glu Gly Ile Tyr
        450                 455

<210> SEQ ID NO 4
<211> LENGTH: 1371
<212> TYPE: DNA
<213> ORGANISM: Artificial Sequence
<220> FEATURE:
<223> OTHER INFORMATION: LsGluDH-A175G

<400> SEQUENCE: 4
atgaccatca ccaccgtttc taacgaacag ctggctaaag aatacgttga cggtgttttc      60
gaacagctga acagcagaa ctgccaccag gctgaattcc tgcaggctgc tgaagaaatc     120
ttcatctctc tggttccggt tttcgttcag cacccggaat acatcaaagc taacatcctg     180
tctcgtatcg ttgaaccgga ccgtatcatc tctttccgtg ttgcttggca ggacgaccac     240
aaccaggttc aggttaaccg tggttaccgt gttcagtact ctaacgttat gggtccgtac     300
aaaggtggtc tgcgtttcca cccgtctgtt aacgaatcta tcatcaaatt cctgggtttc     360
gaacagatct tcaaaaacgc tctgaccggt cagccgatcg tggtggtaa  aggtggttct     420 aacttcgacc cgaaaggtaa atctgactct gaaatcatgc gtttctgcca ggctttcatg     480
accgaactgt accgtcacat cggtccggac gttgacgttc gggtggtga catcggtgtt     540 ggtgctcgtg aagttggtta cctgtggggt cagtacaaac gtctgaccaa agcttctgaa     600
tctggtgttc tgaccggtaa accccgggt acggtggtt ctctggctcg taagaagct     660 accggttacg gtaccgttta cttcgttaac gaaatgctga agacgttaa cgactctttc     720 gaaggtaaaa ccgttgttgt ttctggttct ggtaacgttt ctacctacgc tatcgaaaaa     780
gctcagcagt acggtgctaa agttgttgct tgctctgact cttctggtta catctacgac     840
ccggaaggtc tggacctgga cgttatcaaa gaaatcaaag aagttaaagg tgaccgtatc     900
tctacctacg tttcttaccg tccgaacgct accttcacca acggttgcac cggtatctgg     960
accatcccgt gcgacatcgc tctgccgtgc gctacccaga acgaaatcaa cggtgaatct    1020
```

```
gctcgtaccc tgatctctaa cggtgttaaa gctatcggtg aaggtgctaa catgccgtct    1080
gacctggaag ctatcaacga attcctgaac gctggtgttc tgttcggtcc ggctaaagct    1140
gctaacgctg tggtgttgc tgtttctgct ctggaaatgg ctcaggactc ttctcgtgtt    1200
ttctggtctt tcgaagaagt tgacgctaaa ctgcaccaga tcatgaaaga catctactct    1260
gactctaaag ctgctgctga aaaatacggt ttcccgggta acctggttat gggtgctaac    1320
atcgctggtt tcatcaaagt tgctgacggt atgctgaccg aaggtatcta c             1371
```

<210> SEQ ID NO 5
<211> LENGTH: 457
<212> TYPE: PRT
<213> ORGANISM: Artificial Sequence
<220> FEATURE:
<223> OTHER INFORMATION: LsGluDH-V386A

<400> SEQUENCE: 5

```
Met Thr Ile Thr Thr Val Ser Asn Glu Gln Leu Ala Lys Glu Tyr Val
1               5                   10                  15

Asp Gly Val Phe Glu Gln Leu Lys Gln Gln Asn Cys His Gln Ala Glu
            20                  25                  30

Phe Leu Gln Ala Ala Glu Glu Ile Phe Ile Ser Leu Val Pro Val Phe
        35                  40                  45

Val Gln His Pro Glu Tyr Ile Lys Ala Asn Ile Leu Ser Arg Ile Val
    50                  55                  60

Glu Pro Asp Arg Ile Ile Ser Phe Arg Val Ala Trp Gln Asp Asp His
65                  70                  75                  80

Asn Gln Val Gln Val Asn Arg Gly Tyr Arg Val Gln Tyr Ser Asn Val
                85                  90                  95

Met Gly Pro Tyr Lys Gly Gly Leu Arg Phe His Pro Ser Val Asn Glu
            100                 105                 110

Ser Ile Ile Lys Phe Leu Gly Phe Glu Gln Ile Phe Lys Asn Ala Leu
        115                 120                 125

Thr Gly Gln Pro Ile Gly Gly Gly Lys Gly Gly Ser Asn Phe Asp Pro
    130                 135                 140

Lys Gly Lys Ser Asp Ser Glu Ile Met Arg Phe Cys Gln Ala Phe Met
145                 150                 155                 160

Thr Glu Leu Tyr Arg His Ile Gly Pro Asp Val Asp Val Pro Ala Gly
                165                 170                 175

Asp Ile Gly Val Gly Ala Arg Glu Val Gly Tyr Leu Trp Gly Gln Tyr
            180                 185                 190

Lys Arg Leu Thr Lys Ala Ser Glu Ser Gly Val Leu Thr Gly Lys Thr
        195                 200                 205

Pro Gly Tyr Gly Gly Ser Leu Ala Arg Lys Glu Ala Thr Gly Tyr Gly
    210                 215                 220

Thr Val Tyr Phe Val Asn Glu Met Leu Lys Asp Val Asn Asp Ser Phe
225                 230                 235                 240

Glu Gly Lys Thr Val Val Ser Gly Ser Gly Asn Val Ser Thr Tyr
                245                 250                 255

Ala Ile Glu Lys Ala Gln Gln Tyr Gly Ala Lys Val Val Ala Cys Ser
            260                 265                 270

Asp Ser Ser Gly Tyr Ile Tyr Asp Pro Glu Gly Leu Asp Leu Asp Val
        275                 280                 285

Ile Lys Glu Ile Lys Glu Val Lys Gly Asp Arg Ile Ser Thr Tyr Val
    290                 295                 300
```

```
Ser Tyr Arg Pro Asn Ala Thr Phe Thr Asn Gly Cys Thr Gly Ile Trp
305                 310                 315                 320

Thr Ile Pro Cys Asp Ile Ala Leu Pro Cys Ala Thr Gln Asn Glu Ile
                325                 330                 335

Asn Gly Glu Ser Ala Arg Thr Leu Ile Ser Asn Gly Val Lys Ala Ile
            340                 345                 350

Gly Glu Gly Ala Asn Met Pro Ser Asp Leu Glu Ala Ile Asn Glu Phe
        355                 360                 365

Leu Asn Ala Gly Val Leu Phe Gly Pro Ala Lys Ala Ala Asn Ala Gly
370                 375                 380

Gly Ala Ala Val Ser Ala Leu Glu Met Ala Gln Asp Ser Ser Arg Val
385                 390                 395                 400

Phe Trp Ser Phe Glu Glu Val Asp Ala Lys Leu His Gln Ile Met Lys
                405                 410                 415

Asp Ile Tyr Ser Asp Ser Lys Ala Ala Ala Glu Lys Tyr Gly Phe Pro
                420                 425                 430

Gly Asn Leu Val Met Gly Ala Asn Ile Ala Gly Phe Ile Lys Val Ala
            435                 440                 445

Asp Gly Met Leu Thr Glu Gly Ile Tyr
450                 455

<210> SEQ ID NO 6
<211> LENGTH: 1371
<212> TYPE: DNA
<213> ORGANISM: Artificial Sequence
<220> FEATURE:
<223> OTHER INFORMATION: LsGluDH-V386A

<400> SEQUENCE: 6
atgaccatca ccaccgtttc taacgaacag ctggctaaag aatacgttga cggtgttttc      60
gaacagctga acagcagaa ctgccaccag gctgaattcc tgcaggctgc tgaagaaatc     120
ttcatctctc tggttccggt tttcgttcag cacccggaat acatcaaagc taacatcctg     180
tctcgtatcg ttgaaccgga ccgtatcatc tctttccgtg ttgcttggca ggacgaccac     240
aaccaggttc aggttaaccg tggttaccgt gttcagtact ctaacgttat gggtccgtac     300
aaaggtggtc tgcgtttcca cccgtctgtt aacgaatcta tcatcaaatt cctgggtttc     360
gaacagatct tcaaaaacgc tctgaccggt cagccgatcg gtggtggtaa aggtggttct     420
aacttcgacc cgaaaggtaa atctgactct gaaatcatgc gtttctgcca ggctttcatg     480
accgaactgt accgtcacat cggtccggac gttgacgttc cggctggtga catcggtgtt     540
ggtgctcgtg aagttggtta cctgtggggt cagtacaaac gtctgaccaa gcttctgaa     600
tctggtgttc tgaccggtaa accccgggt acggtggtt ctctggctcg taaagaagct     660
accggttacg gtaccgttta cttcgttaac gaaatgctga agacgttaa cgactctttc     720
gaaggtaaaa ccgttgttgt ttctggttct ggtaacgttt ctaccctacgc tatcgaaaaa     780
gctcagcagt acggtgctaa agttgttgct tgctctgact cttctggtta catctacgac     840
ccggaaggtc tggacctgga cgttatcaaa gaaatcaaag aagttaaagg tgaccgtatc     900
tctacctacg tttcttaccg tccgaacgct accttcacca acggttgcac cggtatctgg     960
accatcccgt gcgacatcgc tctgccgtgc gctacccaga acgaaatcaa cggtgaatct    1020
gctcgtaccc tgatctctaa cggtgttaaa gctatcggtg aaggtgctaa catgccgtct    1080
gacctggaag ctatcaacga attcctgaac gctggtgttc tgttcggtcc ggctaaagct    1140
gctaacgctg gtggtgctgc tgtttctgct ctggaaatgg ctcaggactc ttctcgtgtt    1200
```

```
ttctggtctt tcgaagaagt tgacgctaaa ctgcaccaga tcatgaaaga catctactct    1260
gactctaaag ctgctgctga aaaatacggt ttcccgggta acctggttat gggtgctaac    1320
atcgctggtt tcatcaaagt tgctgacggt atgctgaccg aaggtatcta c             1371
```

<210> SEQ ID NO 7
<211> LENGTH: 457
<212> TYPE: PRT
<213> ORGANISM: Artificial Sequence
<220> FEATURE:
<223> OTHER INFORMATION: LsGluDH-A175G-V386S

<400> SEQUENCE: 7

```
Met Thr Ile Thr Thr Val Ser Asn Glu Gln Leu Ala Lys Glu Tyr Val
1               5                   10                  15

Asp Gly Val Phe Glu Gln Leu Lys Gln Gln Asn Cys His Gln Ala Glu
            20                  25                  30

Phe Leu Gln Ala Ala Glu Glu Ile Phe Ile Ser Leu Val Pro Val Phe
        35                  40                  45

Val Gln His Pro Glu Tyr Ile Lys Ala Asn Ile Leu Ser Arg Ile Val
    50                  55                  60

Glu Pro Asp Arg Ile Ile Ser Phe Arg Val Ala Trp Gln Asp Asp His
65                  70                  75                  80

Asn Gln Val Gln Val Asn Arg Gly Tyr Arg Val Gln Tyr Ser Asn Val
                85                  90                  95

Met Gly Pro Tyr Lys Gly Gly Leu Arg Phe His Pro Ser Val Asn Glu
            100                 105                 110

Ser Ile Ile Lys Phe Leu Gly Phe Glu Gln Ile Phe Lys Asn Ala Leu
        115                 120                 125

Thr Gly Gln Pro Ile Gly Gly Gly Lys Gly Gly Ser Asn Phe Asp Pro
    130                 135                 140

Lys Gly Lys Ser Asp Ser Glu Ile Met Arg Phe Cys Gln Ala Phe Met
145                 150                 155                 160

Thr Glu Leu Tyr Arg His Ile Gly Pro Asp Val Asp Val Pro Gly Gly
                165                 170                 175

Asp Ile Gly Val Gly Ala Arg Glu Val Gly Tyr Leu Trp Gly Gln Tyr
            180                 185                 190

Lys Arg Leu Thr Lys Ala Ser Glu Ser Gly Val Leu Thr Gly Lys Thr
        195                 200                 205

Pro Gly Tyr Gly Gly Ser Leu Ala Arg Lys Glu Ala Thr Gly Tyr Gly
    210                 215                 220

Thr Val Tyr Phe Val Asn Glu Met Leu Lys Asp Val Asn Asp Ser Phe
225                 230                 235                 240

Glu Gly Lys Thr Val Val Ser Gly Ser Gly Asn Val Ser Thr Tyr
                245                 250                 255

Ala Ile Glu Lys Ala Gln Gln Tyr Gly Ala Lys Val Val Ala Cys Ser
            260                 265                 270

Asp Ser Ser Gly Tyr Ile Tyr Asp Pro Glu Gly Leu Asp Leu Asp Val
        275                 280                 285

Ile Lys Glu Ile Lys Glu Val Lys Gly Asp Arg Ile Ser Thr Tyr Val
    290                 295                 300

Ser Tyr Arg Pro Asn Ala Thr Phe Thr Asn Gly Cys Thr Gly Ile Trp
305                 310                 315                 320

Thr Ile Pro Cys Asp Ile Ala Leu Pro Cys Ala Thr Gln Asn Glu Ile
                325                 330                 335
```

Asn Gly Glu Ser Ala Arg Thr Leu Ile Ser Asn Gly Val Lys Ala Ile
            340                 345                 350

Gly Glu Gly Ala Asn Met Pro Ser Asp Leu Glu Ala Ile Asn Glu Phe
        355                 360                 365

Leu Asn Ala Gly Val Leu Phe Gly Pro Ala Lys Ala Asn Ala Gly
370                 375                 380

Gly Ser Ala Val Ser Ala Leu Glu Met Ala Gln Asp Ser Ser Arg Val
385                 390                 395                 400

Phe Trp Ser Phe Glu Glu Val Asp Ala Lys Leu His Gln Ile Met Lys
                405                 410                 415

Asp Ile Tyr Ser Asp Ser Lys Ala Ala Glu Lys Tyr Gly Phe Pro
            420                 425                 430

Gly Asn Leu Val Met Gly Ala Asn Ile Ala Gly Phe Ile Lys Val Ala
            435                 440                 445

Asp Gly Met Leu Thr Glu Gly Ile Tyr
    450                 455

<210> SEQ ID NO 8
<211> LENGTH: 1371
<212> TYPE: DNA
<213> ORGANISM: Artificial Sequence
<220> FEATURE:
<223> OTHER INFORMATION: LsGluDH-A175G-V386S

<400> SEQUENCE: 8

```
atgaccatca ccaccgtttc taacgaacag ctggctaaag aatacgttga cggtgttttc     60
gaacagctga acagcagaa ctgccaccag gctgaattcc tgcaggctgc tgaagaaatc    120
ttcatctctc tggttccggt tttcgttcag cacccggaat acatcaaagc taacatcctg    180
tctcgtatcg ttgaaccgga ccgtatcatc tctttccgtg ttgcttggca ggacgaccac    240
aaccaggttc aggttaaccg tggttaccgt gttcagtact ctaacgttat gggtccgtac    300
aaaggtggtc tgcgtttcca cccgtctgtt aacgaatcta tcatcaaatt cctgggtttc    360
gaacagatct tcaaaaacgc tctgaccggt cagccgatcg tggtggtaa ggtggttct     420
aacttcgacc cgaaaggtaa atctgactct gaaatcatgc gttctgcca ggctttcatg     480
accgaactgt accgtcacat cggtccggac gttgacgttc gggtggtga catcggtgtt     540
ggtgctcgtg aagttggtta cctgtggggt cagtacaaac gtctgaccaa gcttctgaa     600
tctggtgttc tgaccggtaa accccgggt tacggtggtt ctctggctcg taagaagct     660
accggttacg gtaccgttta cttcgttaac gaaatgctga agacgttaa cgactctttc     720
gaaggtaaaa ccgttgttgt ttctggttct ggtaacgttt ctacctacgc tatcgaaaaa    780
gctcagcagt acggtgctaa agttgttgct tgctctgact cttctggtta catctacgac    840
ccggaaggtc tggacctgga cgttatcaaa gaaatcaaag aagttaaagg tgaccgtatc    900
tctacctacg tttcttaccg tccgaacgct accttcacca acggttgcac cggtatctgg    960
accatcccgt gcgacatcgc tctgccgtgc gctacccaga cgaaatcaa cggtgaatct   1020
gctcgtaccc tgatctctaa cggtgttaaa gctatcggtg aaggtgctaa catgccgtct   1080
gacctggaag ctatcaacga attcctgaac gctggtgttc tgttcggtcc ggctaaagct   1140
gctaacgctg gtggttctgc tgtttctgct ctggaaatgg ctcaggactc ttctcgtgtt   1200
ttctggtctt tcgaagaagt tgacgctaaa ctgcaccaga tcatgaaaga catctactct   1260
gactctaaag ctgctgctga aaaatacggt ttcccgggta acctggttat gggtgctaac   1320
```
atcgctggtt tcatcaaagt tgctgacggt atgctgaccg aaggtatcta c        1371

<210> SEQ ID NO 9
<211> LENGTH: 457
<212> TYPE: PRT
<213> ORGANISM: Artificial Sequence
<220> FEATURE:
<223> OTHER INFORMATION: LsGluDH-A175G-V386A

<400> SEQUENCE: 9

```
Met Thr Ile Thr Thr Val Ser Asn Glu Gln Leu Ala Lys Glu Tyr Val
1               5                   10                  15

Asp Gly Val Phe Glu Gln Leu Lys Gln Gln Asn Cys His Gln Ala Glu
            20                  25                  30

Phe Leu Gln Ala Ala Glu Glu Ile Phe Ile Ser Leu Val Pro Val Phe
        35                  40                  45

Val Gln His Pro Glu Tyr Ile Lys Ala Asn Ile Leu Ser Arg Ile Val
    50                  55                  60

Glu Pro Asp Arg Ile Ile Ser Phe Arg Val Ala Trp Gln Asp Asp His
65                  70                  75                  80

Asn Gln Val Gln Val Asn Arg Gly Tyr Arg Val Gln Tyr Ser Asn Val
                85                  90                  95

Met Gly Pro Tyr Lys Gly Gly Leu Arg Phe His Pro Ser Val Asn Glu
            100                 105                 110

Ser Ile Ile Lys Phe Leu Gly Phe Glu Gln Ile Phe Lys Asn Ala Leu
        115                 120                 125

Thr Gly Gln Pro Ile Gly Gly Gly Lys Gly Ser Asn Phe Asp Pro
    130                 135                 140

Lys Gly Lys Ser Asp Ser Glu Ile Met Arg Phe Cys Gln Ala Phe Met
145                 150                 155                 160

Thr Glu Leu Tyr Arg His Ile Gly Pro Asp Val Asp Val Pro Gly Gly
                165                 170                 175

Asp Ile Gly Val Gly Ala Arg Glu Val Gly Tyr Leu Trp Gly Gln Tyr
            180                 185                 190

Lys Arg Leu Thr Lys Ala Ser Glu Ser Gly Val Leu Thr Gly Lys Thr
        195                 200                 205

Pro Gly Tyr Gly Gly Ser Leu Ala Arg Lys Glu Ala Thr Gly Tyr Gly
    210                 215                 220

Thr Val Tyr Phe Val Asn Glu Met Leu Lys Asp Val Asn Asp Ser Phe
225                 230                 235                 240

Glu Gly Lys Thr Val Val Ser Gly Ser Gly Asn Val Ser Thr Tyr
                245                 250                 255

Ala Ile Glu Lys Ala Gln Gln Tyr Gly Ala Lys Val Val Ala Cys Ser
            260                 265                 270

Asp Ser Ser Gly Tyr Ile Tyr Asp Pro Glu Gly Leu Asp Leu Asp Val
        275                 280                 285

Ile Lys Glu Ile Lys Glu Val Lys Gly Asp Arg Ile Ser Thr Tyr Val
    290                 295                 300

Ser Tyr Arg Pro Asn Ala Thr Phe Thr Asn Gly Cys Thr Gly Ile Trp
305                 310                 315                 320

Thr Ile Pro Cys Asp Ile Ala Leu Pro Cys Ala Thr Gln Asn Glu Ile
                325                 330                 335

Asn Gly Glu Ser Ala Arg Thr Leu Ile Ser Asn Gly Val Lys Ala Ile
            340                 345                 350

Gly Glu Gly Ala Asn Met Pro Ser Asp Leu Glu Ala Ile Asn Glu Phe
```

```
                     355                 360                 365
Leu Asn Ala Gly Val Leu Phe Gly Pro Ala Lys Ala Ala Asn Ala Gly
            370                 375                 380
Gly Ala Ala Val Ser Ala Leu Glu Met Ala Gln Asp Ser Ser Arg Val
385                 390                 395                 400
Phe Trp Ser Phe Glu Glu Val Asp Ala Lys Leu His Gln Ile Met Lys
                405                 410                 415
Asp Ile Tyr Ser Asp Ser Lys Ala Ala Ala Glu Lys Tyr Gly Phe Pro
            420                 425                 430
Gly Asn Leu Val Met Gly Ala Asn Ile Ala Gly Phe Ile Lys Val Ala
            435                 440                 445
Asp Gly Met Leu Thr Glu Gly Ile Tyr
        450                 455

<210> SEQ ID NO 10
<211> LENGTH: 1371
<212> TYPE: DNA
<213> ORGANISM: Artificial Sequence
<220> FEATURE:
<223> OTHER INFORMATION: LsGluDH-A175G-V386A

<400> SEQUENCE: 10
```

| | | | | | |
|---|---|---|---|---|---|
| atgaccatca | ccaccgtttc | taacgaacag | ctggctaaag | aatacgttga | cggtgttttc    60 |
| gaacagctga | acagcagaa | ctgccaccag | gctgaattcc | tgcaggctgc | tgaagaaatc   120 |
| ttcatctctc | tggttccggt | tttcgttcag | cacccggaat | acatcaaagc | taacatcctg   180 |
| tctcgtatcg | ttgaaccgga | ccgtatcatc | tctttccgtg | ttgcttggca | ggacgaccac   240 |
| aaccaggttc | aggttaaccg | tggttaccgt | gttcagtact | ctaacgttat | gggtccgtac   300 |
| aaaggtggtc | tgcgtttcca | cccgtctgtt | aacgaatcta | tcatcaaatt | cctgggtttc   360 |
| gaacagatct | tcaaaaacgc | tctgaccggt | cagccgatcg | gtggtggtaa | aggtggttct   420 |
| aacttcgacc | cgaaaggtaa | atctgactct | gaaatcatgc | gtttctgcca | ggctttcatg   480 |
| accgaactgt | accgtcacat | cggtccggac | gttgacgttc | cgggtggtga | catcggtgtt   540 |
| ggtgctcgtg | aagttggtta | cctgtggggt | cagtacaaac | gtctgaccaa | gcttctgaa    600 |
| tctggtgttc | tgaccggtaa | accccgggt | tacggtggtt | ctctggctcg | taagaagct    660 |
| accggttacg | gtaccgttta | cttcgttaac | gaaatgctga | agacgttaa  | cgactctttc   720 |
| gaaggtaaaa | ccgttgttgt | ttctggttct | ggtaacgttt | ctacctacgc | tatcgaaaaa   780 |
| gctcagcagt | acggtgctaa | agttgttgct | tgctctgact | cttctggtta | catctacgac   840 |
| ccggaaggtc | tggacctgga | cgttatcaaa | gaaatcaaag | aagttaaagg | tgaccgtatc   900 |
| tctacctacg | tttcttaccg | tccgaacgct | accttcacca | acggttgcac | cggtatctgg   960 |
| accatcccgt | gcgacatcgc | tctgccgtgc | gctacccaga | cgaaatcaa  | cggtgaatct  1020 |
| gctcgtaccc | tgatctctaa | cggtgttaaa | gctatcggtg | aaggtgctaa | catgccgtct  1080 |
| gacctggaag | ctatcaacga | attcctgaac | gctggtgttc | tgttcggtcc | ggctaaagct  1140 |
| gctaacgctg | gtggtgctgc | tgtttctgct | ctggaaatgg | ctcaggactc | ttctcgtgtt  1200 |
| ttctggtctt | tcgaagaagt | tgacgctaaa | ctgcaccaga | tcatgaaaga | catctactct  1260 |
| gactctaaag | ctgctgctga | aaaatacggt | ttcccgggta | acctggttat | gggtgctaac  1320 |
| atcgctggtt | tcatcaaagt | tgctgacggt | atgctgaccg | aaggtatcta | c            1371 |

```
<210> SEQ ID NO 11
<211> LENGTH: 449
```

<212> TYPE: PRT
<213> ORGANISM: Pseudomonas putida

<400> SEQUENCE: 11

```
Met Ser Thr Met Ile Glu Ser Val Asp Asn Phe Leu Ala Arg Leu Lys
1               5                   10                  15

Gln Arg Asp Pro Gly Gln Pro Glu Phe His Gln Ala Val Glu Val
            20                  25                  30

Leu Arg Thr Leu Trp Pro Phe Leu Glu Ala Asn Pro His Tyr Leu Gln
        35                  40                  45

Ser Gly Ile Leu Glu Arg Met Val Pro Glu Arg Ala Val Leu Phe
    50                  55                  60

Arg Val Ser Trp Val Asp Asp Gln Gly Lys Val Gln Val Asn Arg Gly
65                  70                  75                  80

Tyr Arg Ile Gln Met Ser Ser Ala Ile Gly Pro Tyr Lys Gly Gly Leu
                85                  90                  95

Arg Phe His Pro Ser Val Asn Leu Ser Val Leu Lys Phe Leu Ala Phe
            100                 105                 110

Glu Gln Val Phe Lys Asn Ser Leu Thr Ser Leu Pro Met Gly Gly Gly
        115                 120                 125

Lys Gly Gly Ser Asp Phe Asp Pro Lys Gly Lys Ser Asp Ala Glu Val
    130                 135                 140

Met Arg Phe Cys Gln Ala Phe Met Ser Glu Leu Tyr Arg His Ile Gly
145                 150                 155                 160

Ala Asp Cys Asp Val Pro Ala Gly Asp Ile Gly Val Gly Ala Arg Glu
                165                 170                 175

Ile Gly Phe Met Phe Gly Gln Tyr Lys Arg Leu Ala Asn Gln Phe Thr
            180                 185                 190

Ser Val Leu Thr Gly Lys Gly Met Thr Tyr Gly Gly Ser Leu Ile Arg
        195                 200                 205

Pro Glu Ala Thr Gly Tyr Gly Cys Val Tyr Phe Ala Glu Glu Met Leu
    210                 215                 220

Lys Arg Gln Asp Lys Arg Ile Asp Gly Arg Arg Val Ala Val Ser Gly
225                 230                 235                 240

Ser Gly Asn Val Ala Gln Tyr Ala Ala Arg Lys Val Met Asp Leu Gly
                245                 250                 255

Gly Lys Val Ile Ser Leu Ser Asp Ser Glu Gly Thr Leu Tyr Ala Glu
            260                 265                 270

Ala Gly Leu Thr Asp Ala Gln Trp Asp Ala Leu Met Glu Leu Lys Asn
        275                 280                 285

Val Lys Arg Gly Arg Ile Ser Glu Leu Ala Gly Gln Phe Gly Leu Glu
    290                 295                 300

Phe Arg Lys Gly Gln Thr Pro Trp Ser Leu Pro Cys Asp Ile Ala Leu
305                 310                 315                 320

Pro Cys Ala Thr Gln Asn Glu Leu Gly Ala Glu Asp Ala Arg Thr Leu
                325                 330                 335

Leu Arg Asn Gly Cys Ile Cys Val Ala Glu Gly Ala Asn Met Pro Thr
            340                 345                 350

Thr Leu Glu Ala Val Asp Ile Phe Leu Asp Ala Gly Ile Leu Tyr Ala
        355                 360                 365

Pro Gly Lys Ala Ser Asn Ala Gly Gly Val Ala Val Ser Gly Leu Glu
    370                 375                 380

Met Ser Gln Asn Ala Met Arg Leu Leu Trp Thr Ala Gly Glu Val Asp
385                 390                 395                 400
```

Ser Lys Leu His Asn Ile Met Gln Ser Ile His His Ala Cys Val His
                405                 410                 415

Tyr Gly Glu Glu Ala Asp Gly Arg Ile Asn Tyr Val Lys Gly Ala Asn
            420                 425                 430

Ile Ala Gly Phe Val Lys Val Ala Asp Ala Met Leu Ala Gln Gly Val
        435                 440                 445

Val

<210> SEQ ID NO 12
<211> LENGTH: 1347
<212> TYPE: DNA
<213> ORGANISM: Pseudomonas putida

<400> SEQUENCE: 12

```
atgtctacca tgatcgaatc tgttgacaac ttcctggctc gtctgaaaca gcgtgacccg      60
ggtcagccgg aattccacca ggctgttgaa gaagttctgc gtaccctgtg gccgttcctg     120
gaagctaacc cgcactacct gcagtctggt atcctggaac gtatggttga accggaacgt     180
gctgttctgt ccgtgtttc ttgggttgac gaccagggta agttcaggt taaccgtggt      240
taccgtatcc agatgtcttc tgctatcggt ccgtacaaag gtggtctgcg tttccacccg     300
tctgttaacc tgtctgttct gaaattcctg gctttcgaac aggttttcaa aaactctctg     360
acctctctgc cgatgggtgg tggtaaaggt ggttctgact cgacccgaa aggtaaatct      420
gacgctgaag ttatgcgttt ctgccaggct ttcatgtctg aactgtaccg tcacatcggt     480
gctgactgcg acgttccggc tggtgacatc ggtgttggtg ctcgtgaaat cggtttcatg     540
ttcggtcagt acaaacgtct ggctaaccag ttcacctctg ttctgaccgg taaaggtatg     600
acctacggtg ttctctgat ccgtccggaa gctaccggtt acgttgcgt ttacttcgct      660
gaagaaatgc tgaaacgtca ggacaaacgt atcgacggtc gtcgtgttgc tgtttctggt     720
tctggtaacg ttgctcagta cgctgctcgt aaagttatgg acctgggtgg taaagttatc     780
tctctgtctg actctgaagg taccctgtac gctgaagctg gtctgaccga cgctcagtgg     840
gacgctctga tggaactgaa aaacgttaaa cgtggtcgta tctctgaact ggctggtcag     900
ttcggtctgg aattccgtaa aggtcagacc ccgtggtctc tgccgtgcga catcgctctg     960
ccgtgcgcta cccagaacga actgggtgct gaagacgctc gtaccctgct gcgtaacggt    1020
tgcatctgcg ttgctgaagg tgctaacatg ccgaccaccc tggaagctgt tgacatcttc    1080
ctggacgctg gtatcctgta cgctccgggt aaagcttcta cgctggtgg tgttgctgtt    1140
tctggtctgg aaatgtctca gaacgctatg cgtctgctgt ggaccgctgg tgaagttgac    1200
tctaaactgc acaacatcat gcagtctatc caccacgctt gcgttcacta cggtgaagaa    1260
gctgacggtc gtatcaacta cgttaaaggt gctaacatcg ctggtttcgt taagttgct    1320
gacgctatgc tggctcaggg tgttgtt                                        1347
```

<210> SEQ ID NO 13
<211> LENGTH: 449
<212> TYPE: PRT
<213> ORGANISM: Artificial Sequence
<220> FEATURE:
<223> OTHER INFORMATION: PpGluDH-A167G

<400> SEQUENCE: 13

Met Ser Thr Met Ile Glu Ser Val Asp Asn Phe Leu Ala Arg Leu Lys
1               5                   10                  15

-continued

Gln Arg Asp Pro Gly Gln Pro Glu Phe His Gln Ala Val Glu Val
            20                  25                  30

Leu Arg Thr Leu Trp Pro Phe Leu Glu Ala Asn Pro His Tyr Leu Gln
        35                  40                  45

Ser Gly Ile Leu Glu Arg Met Val Glu Pro Glu Arg Ala Val Leu Phe
    50                  55                  60

Arg Val Ser Trp Val Asp Asp Gln Gly Lys Val Gln Val Asn Arg Gly
65                  70                  75                  80

Tyr Arg Ile Gln Met Ser Ser Ala Ile Gly Pro Tyr Lys Gly Gly Leu
                85                  90                  95

Arg Phe His Pro Ser Val Asn Leu Ser Val Leu Lys Phe Leu Ala Phe
            100                 105                 110

Glu Gln Val Phe Lys Asn Ser Leu Thr Ser Leu Pro Met Gly Gly Gly
        115                 120                 125

Lys Gly Gly Ser Asp Phe Asp Pro Lys Gly Lys Ser Asp Ala Glu Val
    130                 135                 140

Met Arg Phe Cys Gln Ala Phe Met Ser Glu Leu Tyr Arg His Ile Gly
145                 150                 155                 160

Ala Asp Cys Asp Val Pro Gly Gly Asp Ile Gly Val Gly Ala Arg Glu
                165                 170                 175

Ile Gly Phe Met Phe Gly Gln Tyr Lys Arg Leu Ala Asn Gln Phe Thr
            180                 185                 190

Ser Val Leu Thr Gly Lys Gly Met Thr Tyr Gly Gly Ser Leu Ile Arg
        195                 200                 205

Pro Glu Ala Thr Gly Tyr Gly Cys Val Tyr Phe Ala Glu Glu Met Leu
    210                 215                 220

Lys Arg Gln Asp Lys Arg Ile Asp Gly Arg Arg Val Ala Val Ser Gly
225                 230                 235                 240

Ser Gly Asn Val Ala Gln Tyr Ala Ala Arg Lys Val Met Asp Leu Gly
                245                 250                 255

Gly Lys Val Ile Ser Leu Ser Asp Ser Glu Gly Thr Leu Tyr Ala Glu
            260                 265                 270

Ala Gly Leu Thr Asp Ala Gln Trp Asp Ala Leu Met Glu Leu Lys Asn
        275                 280                 285

Val Lys Arg Gly Arg Ile Ser Glu Leu Ala Gly Gln Phe Gly Leu Glu
    290                 295                 300

Phe Arg Lys Gly Gln Thr Pro Trp Ser Leu Pro Cys Asp Ile Ala Leu
305                 310                 315                 320

Pro Cys Ala Thr Gln Asn Glu Leu Gly Ala Glu Asp Ala Arg Thr Leu
                325                 330                 335

Leu Arg Asn Gly Cys Ile Cys Val Ala Glu Gly Ala Asn Met Pro Thr
            340                 345                 350

Thr Leu Glu Ala Val Asp Ile Phe Leu Asp Ala Gly Ile Leu Tyr Ala
        355                 360                 365

Pro Gly Lys Ala Ser Asn Ala Gly Gly Val Ala Val Ser Gly Leu Glu
    370                 375                 380

Met Ser Gln Asn Ala Met Arg Leu Leu Trp Thr Ala Gly Glu Val Asp
385                 390                 395                 400

Ser Lys Leu His Asn Ile Met Gln Ser Ile His His Ala Cys Val His
                405                 410                 415

Tyr Gly Glu Glu Ala Asp Gly Arg Ile Asn Tyr Val Lys Gly Ala Asn
            420                 425                 430

Ile Ala Gly Phe Val Lys Val Ala Asp Ala Met Leu Ala Gln Gly Val

Val

<210> SEQ ID NO 14
<211> LENGTH: 1347
<212> TYPE: DNA
<213> ORGANISM: Artificial Sequence
<220> FEATURE:
<223> OTHER INFORMATION: PpGluDH-A167G

<400> SEQUENCE: 14

```
atgtctacca tgatcgaatc tgttgacaac ttcctggctc gtctgaaaca gcgtgacccg      60
ggtcagccgg aattccacca ggctgttgaa gaagttctgc gtaccctgtg gccgttcctg     120
gaagctaacc cgcactacct gcagtctggt atcctggaac gtatggttga accggaacgt     180
gctgttctgt tccgtgtttc ttgggttgac gaccagggta agttcaggt taaccgtggt      240
taccgtatcc agatgtcttc tgctatcggt ccgtacaaag tggtctgcg tttccacccg      300
tctgttaacc tgtctgttct gaaattcctg gctttcgaac aggttttcaa aaactctctg     360
acctctctgc cgatgggtgg tggtaaaggt ggttctgact cgacccgaa aggtaaatct      420
gacgctgaag ttatgcgttt ctgccaggct ttcatgtctg aactgtaccg tcacatcggt     480
gctgactgcg acgttccggg tggtgacatc ggtgttggtg ctcgtgaaat cggtttcatg     540
ttcggtcagt acaaacgtct ggctaaccag ttcacctctg ttctgaccgg taaaggtatg     600
acctacggtg ttctctctga tccgtccgga gctaccggtt acggttgcgt ttacttcgct     660
gaagaaatgc tgaaacgtca ggacaaacgt atcgacggtc gtcgtgttgc tgtttctggt     720
tctggtaacg ttgctcagta cgctgctcgt aaagttatgg acctgggtgg taaagttatc     780
tctctgtctg actctgaagg taccctgtac gctgaagctg gtctgaccga cgctcagtgg     840
gacgctctga tggaactgaa aaacgttaaa cgtggtcgta tctctgaact ggctggtcag     900
ttcggtctgg aattccgtaa aggtcagacc cgtggtctc tgccgtgcga catcgctctg      960
ccgtgcgcta cccagaacga actgggtgct gaagacgctc gtaccctgct gcgtaacggt    1020
tgcatctgcg ttgctgaagg tgctaacatg ccgaccaccc tggaagctgt tgacatcttc    1080
ctggacgctg gtatcctgta cgctccgggt aaagcttcta cgctggtgg tgttgctgtt    1140
tctggtctgg aaatgtctca gaacgctatg cgtctgctgt ggaccgctgg tgaagttgac    1200
tctaaactgc acaacatcat gcagtctatc caccacgctt gcgttcacta cggtgaagaa    1260
gctgacggtc gtatcaacta cgttaaaggt gctaacatcg ctggtttcgt taaagttgct    1320
gacgctatgc tggctcaggg tgttgtt                                        1347
```

<210> SEQ ID NO 15
<211> LENGTH: 449
<212> TYPE: PRT
<213> ORGANISM: Artificial Sequence
<220> FEATURE:
<223> OTHER INFORMATION: PpGluDH-V378A

<400> SEQUENCE: 15

Met Ser Thr Met Ile Glu Ser Val Asp Asn Phe Leu Ala Arg Leu Lys
1               5                   10                  15

Gln Arg Asp Pro Gly Gln Pro Glu Phe His Gln Ala Val Glu Glu Val
            20                  25                  30

Leu Arg Thr Leu Trp Pro Phe Leu Glu Ala Asn Pro His Tyr Leu Gln
        35                  40                  45

-continued

```
Ser Gly Ile Leu Glu Arg Met Val Glu Pro Glu Arg Ala Val Leu Phe
    50                  55                  60
Arg Val Ser Trp Val Asp Asp Gln Gly Lys Val Gln Val Asn Arg Gly
 65                  70                  75                  80
Tyr Arg Ile Gln Met Ser Ser Ala Ile Gly Pro Tyr Lys Gly Gly Leu
                 85                  90                  95
Arg Phe His Pro Ser Val Asn Leu Ser Val Leu Lys Phe Leu Ala Phe
            100                 105                 110
Glu Gln Val Phe Lys Asn Ser Leu Thr Ser Leu Pro Met Gly Gly Gly
        115                 120                 125
Lys Gly Gly Ser Asp Phe Asp Pro Lys Gly Lys Ser Asp Ala Glu Val
130                 135                 140
Met Arg Phe Cys Gln Ala Phe Met Ser Glu Leu Tyr Arg His Ile Gly
145                 150                 155                 160
Ala Asp Cys Asp Val Pro Ala Gly Asp Ile Gly Val Gly Ala Arg Glu
                165                 170                 175
Ile Gly Phe Met Phe Gly Gln Tyr Lys Arg Leu Ala Asn Gln Phe Thr
            180                 185                 190
Ser Val Leu Thr Gly Lys Gly Met Thr Tyr Gly Gly Ser Leu Ile Arg
        195                 200                 205
Pro Glu Ala Thr Gly Tyr Gly Cys Val Tyr Phe Ala Glu Glu Met Leu
210                 215                 220
Lys Arg Gln Asp Lys Arg Ile Asp Gly Arg Val Ala Val Ser Gly
225                 230                 235                 240
Ser Gly Asn Val Ala Gln Tyr Ala Ala Arg Lys Val Met Asp Leu Gly
                245                 250                 255
Gly Lys Val Ile Ser Leu Ser Asp Ser Glu Gly Thr Leu Tyr Ala Glu
            260                 265                 270
Ala Gly Leu Thr Asp Ala Gln Trp Asp Ala Leu Met Glu Leu Lys Asn
        275                 280                 285
Val Lys Arg Gly Arg Ile Ser Glu Leu Ala Gly Gln Phe Gly Leu Glu
290                 295                 300
Phe Arg Lys Gly Gln Thr Pro Trp Ser Leu Pro Cys Asp Ile Ala Leu
305                 310                 315                 320
Pro Cys Ala Thr Gln Asn Glu Leu Gly Ala Glu Asp Ala Arg Thr Leu
                325                 330                 335
Leu Arg Asn Gly Cys Ile Cys Val Ala Glu Gly Ala Asn Met Pro Thr
            340                 345                 350
Thr Leu Glu Ala Val Asp Ile Phe Leu Asp Ala Gly Ile Leu Tyr Ala
        355                 360                 365
Pro Gly Lys Ala Ser Asn Ala Gly Gly Ala Ala Val Ser Gly Leu Glu
370                 375                 380
Met Ser Gln Asn Ala Met Arg Leu Leu Trp Thr Ala Gly Glu Val Asp
385                 390                 395                 400
Ser Lys Leu His Asn Ile Met Gln Ser Ile His His Ala Cys Val His
                405                 410                 415
Tyr Gly Glu Glu Ala Asp Gly Arg Ile Asn Tyr Val Lys Gly Ala Asn
            420                 425                 430
Ile Ala Gly Phe Val Lys Val Ala Asp Ala Met Leu Ala Gln Gly Val
        435                 440                 445
Val

<210> SEQ ID NO 16
```

<211> LENGTH: 1347
<212> TYPE: DNA
<213> ORGANISM: Artificial Sequence
<220> FEATURE:
<223> OTHER INFORMATION: PpGluDH-V378A

<400> SEQUENCE: 16

```
atgtctacca tgatcgaatc tgttgacaac ttcctggctc gtctgaaaca gcgtgacccg      60
ggtcagccgg aattccacca ggctgttgaa gaagttctgc gtaccctgtg gccgttcctg     120
gaagctaacc cgcactacct gcagtctggt atcctggaac gtatggttga accggaacgt     180
gctgttctgt tccgtgtttc ttgggttgac gaccagggta agttcaggt taaccgtggt     240
taccgtatcc agatgtcttc tgctatcggt ccgtacaaag gtggtctgcg tttccacccg     300
tctgttaacc tgtctgttct gaaattcctg gctttcgaac aggttttcaa aaactctctg     360
acctctctgc cgatgggtgg tggtaaaggt ggttctgact cgacccgaa aggtaaatct     420
gacgctgaag ttatgcgttt ctgccaggct ttcatgtctg aactgtaccg tcacatcggt     480
gctgactgcg acgttccggc tggtgacatc ggtgttggtg ctcgtgaaat cggtttcatg     540
ttcggtcagt acaaacgtct ggctaaccag ttcacctctg ttctgaccgg taaaggtatg     600
acctacggtg gttctctgat ccgtccggaa gctaccggtt acgttgcgt ttacttcgct     660
gaagaaatgc tgaaacgtca ggacaaacgt atcgacggtc gtcgtgttgc tgtttctggt     720
tctggtaacg ttgctcagta cgctgctcgt aaagttatgg acctgggtgg taaagttatc     780
tctctgtctg actctgaagg taccctgtac gctgaagctg gtctgaccga cgctcagtgg     840
gacgctctga tggaactgaa aaacgttaaa cgtggtcgta tctctgaact ggctggtcag     900
ttcggtctgg aattccgtaa aggtcagacc ccgtggtctc tgccgtgcga catcgctctg     960
ccgtgcgcta cccagaacga actgggtgct gaagacgctc gtaccctgct gcgtaacggt    1020
tgcatctgcg ttgctgaagg tgctaacatg ccgaccaccc tggaagctgt tgacatcttc    1080
ctggacgctg gtatcctgta cgctccgggt aaagcttcta cgctggtgg tgctgctgtt    1140
tctggtctgg aaatgtctca gaacgctatg cgtctgctgt ggaccgctgg tgaagttgac    1200
tctaaactgc acaacatcat gcagtctatc caccacgctt gcgttcacta cggtgaagaa    1260
gctgacggtc gtatcaacta cgttaaaggt gctaacatcg ctggtttcgt taaagttgct    1320
gacgctatgc tggctcaggg tgttgtt                                         1347
```

<210> SEQ ID NO 17
<211> LENGTH: 449
<212> TYPE: PRT
<213> ORGANISM: Artificial Sequence
<220> FEATURE:
<223> OTHER INFORMATION: PpGluDH-A167G-V378A

<400> SEQUENCE: 17

```
Met Ser Thr Met Ile Glu Ser Val Asp Asn Phe Leu Ala Arg Leu Lys
1               5                   10                  15

Gln Arg Asp Pro Gly Gln Pro Glu Phe His Gln Ala Val Glu Glu Val
            20                  25                  30

Leu Arg Thr Leu Trp Pro Phe Leu Glu Ala Asn Pro His Tyr Leu Gln
        35                  40                  45

Ser Gly Ile Leu Glu Arg Met Val Glu Pro Glu Arg Ala Val Leu Phe
    50                  55                  60

Arg Val Ser Trp Val Asp Asp Gln Gly Lys Val Gln Val Asn Arg Gly
65                  70                  75                  80
```

```
Tyr Arg Ile Gln Met Ser Ser Ala Ile Gly Pro Tyr Lys Gly Gly Leu
                    85                  90                  95

Arg Phe His Pro Ser Val Asn Leu Ser Val Leu Lys Phe Leu Ala Phe
            100                 105                 110

Glu Gln Val Phe Lys Asn Ser Leu Thr Ser Leu Pro Met Gly Gly Gly
        115                 120                 125

Lys Gly Gly Ser Asp Phe Asp Pro Lys Gly Lys Ser Asp Ala Glu Val
130                 135                 140

Met Arg Phe Cys Gln Ala Phe Met Ser Glu Leu Tyr Arg His Ile Gly
145                 150                 155                 160

Ala Asp Cys Asp Val Pro Gly Gly Asp Ile Gly Val Gly Ala Arg Glu
                165                 170                 175

Ile Gly Phe Met Phe Gly Gln Tyr Lys Arg Leu Ala Asn Gln Phe Thr
            180                 185                 190

Ser Val Leu Thr Gly Lys Gly Met Thr Tyr Gly Gly Ser Leu Ile Arg
        195                 200                 205

Pro Glu Ala Thr Gly Tyr Gly Cys Val Tyr Phe Ala Glu Glu Met Leu
    210                 215                 220

Lys Arg Gln Asp Lys Arg Ile Asp Gly Arg Arg Val Ala Val Ser Gly
225                 230                 235                 240

Ser Gly Asn Val Ala Gln Tyr Ala Ala Arg Lys Val Met Asp Leu Gly
                245                 250                 255

Gly Lys Val Ile Ser Leu Ser Asp Ser Glu Gly Thr Leu Tyr Ala Glu
            260                 265                 270

Ala Gly Leu Thr Asp Ala Gln Trp Asp Ala Leu Met Glu Leu Lys Asn
        275                 280                 285

Val Lys Arg Gly Arg Ile Ser Glu Leu Ala Gly Gln Phe Gly Leu Glu
    290                 295                 300

Phe Arg Lys Gly Gln Thr Pro Trp Ser Leu Pro Cys Asp Ile Ala Leu
305                 310                 315                 320

Pro Cys Ala Thr Gln Asn Glu Leu Gly Ala Glu Asp Ala Arg Thr Leu
                325                 330                 335

Leu Arg Asn Gly Cys Ile Cys Val Ala Glu Gly Ala Asn Met Pro Thr
            340                 345                 350

Thr Leu Glu Ala Val Asp Ile Phe Leu Asp Ala Gly Ile Leu Tyr Ala
        355                 360                 365

Pro Gly Lys Ala Ser Asn Ala Gly Gly Ala Ala Val Ser Gly Leu Glu
    370                 375                 380

Met Ser Gln Asn Ala Met Arg Leu Leu Trp Thr Ala Gly Glu Val Asp
385                 390                 395                 400

Ser Lys Leu His Asn Ile Met Gln Ser Ile His His Ala Cys Val His
                405                 410                 415

Tyr Gly Glu Glu Ala Asp Gly Arg Ile Asn Tyr Val Lys Gly Ala Asn
            420                 425                 430

Ile Ala Gly Phe Val Lys Val Ala Asp Ala Met Leu Ala Gln Gly Val
        435                 440                 445

Val

<210> SEQ ID NO 18
<211> LENGTH: 1347
<212> TYPE: DNA
<213> ORGANISM: Artificial Sequence
<220> FEATURE:
<223> OTHER INFORMATION: PpGluDH-A167G-V378A
```

```
<400> SEQUENCE: 18
atgtctacca tgatcgaatc tgttgacaac ttcctggctc gtctgaaaca gcgtgacccg      60
ggtcagccgg aattccacca ggctgttgaa gaagttctgc gtaccctgtg gccgttcctg     120
gaagctaacc cgcactacct gcagtctggt atcctggaac gtatggttga accggaacgt     180
gctgttctgt tccgtgtttc ttgggttgac gaccagggta aagttcaggt taaccgtggt     240
taccgtatcc agatgtcttc tgctatcggt ccgtacaaag gtggtctgcg tttccacccg     300
tctgttaacc tgtctgttct gaaattcctg gctttcgaac aggttttcaa aaactctctg     360
acctctctgc cgatgggtgg tggtaaaggt ggttctgact tcgacccgaa aggtaaatct     420
gacgctgaag ttatgcgttt ctgccaggct ttcatgtctg aactgtaccg tcacatcggt     480
gctgactgcg acgttccggg tggtgacatc ggtgttggtg ctcgtgaaat cggtttcatg     540
ttcggtcagt acaaacgtct ggctaaccag ttcacctctg ttctgaccgg taaaggtatg     600
acctacggtg ttctctgat ccgtccggaa gctaccggtt acggttgcgt ttacttcgct     660
gaagaaatgc tgaaacgtca ggacaaacgt atcgacggtc gtcgtgttgc tgtttctggt     720
tctggtaacg ttgctcagta cgctgctcgt aaagttatgg acctgggtgg taaagttatc     780
tctctgtctg actctgaagg tacccctgtac gctgaagctg gtctgaccga cgctcagtgg     840
gacgctctga tggaactgaa aaacgttaaa cgtggtcgta tctctgaact ggctggtcag     900
ttcggtctgg aattccgtaa aggtcagacc ccgtggtctc tgccgtgcga catcgctctg     960
ccgtgcgcta cccagaacga actgggtgct gaagacgctc gtaccctgct gcgtaacggt    1020
tgcatctgcg ttgctgaagg tgctaacatg ccgaccaccc tggaagctgt tgacatcttc    1080
ctggacgctg gtatcctgta cgctccgggt aaagcttcta acgctggtgg tgctgctgtt    1140
tctggtctgg aaatgtctca gaacgctatg cgtctgctgt ggaccgctgg tgaagttgac    1200
tctaaactgc acaacatcat gcagtctatc caccacgctt gcgttcacta cggtgaagaa    1260
gctgacggtc gtatcaacta cgttaaaggt gctaacatcg ctggtttcgt taaagttgct    1320
gacgctatgc tggctcaggg tgttgtt                                        1347
```